(12) United States Patent
Mazzocchi et al.

(10) Patent No.: US 7,896,889 B2
(45) Date of Patent: Mar. 1, 2011

(54) TRAJECTORY GUIDE WITH ANGLED OR PATTERNED LUMENS OR HEIGHT ADJUSTMENT

(75) Inventors: Rudy A. Mazzocchi, Melbourne, FL (US); Matthew S. Solar, Indialantic, FL (US); Thomas B. Freeman, Tampa, FL (US)

(73) Assignees: Medtronic, Inc., Minneapolis, MN (US); University of South Florida Research Foundation, Inc., Tampa, FL (US)

( * ) Notice: Subject to any disclaimer, the term of this patent is extended or adjusted under 35 U.S.C. 154(b) by 1341 days.

(21) Appl. No.: 10/370,090

(22) Filed: Feb. 20, 2003

(65) Prior Publication Data

US 2004/0167543 A1    Aug. 26, 2004

(51) Int. Cl.
*A61B 19/00* (2006.01)
(52) U.S. Cl. ............................................. 606/130
(58) Field of Classification Search ............ 606/87, 606/96, 98, 129, 54, 130; 600/386, 417, 600/429

See application file for complete search history.

(56) References Cited

U.S. PATENT DOCUMENTS

| | | |
|---|---|---|
| 431,187 A | 7/1890 | Foster |
| 438,801 A | 10/1890 | Delehanty |
| 873,009 A | 12/1907 | Baxter |
| 1,129,333 A | 2/1915 | Clarke |
| 1,664,210 A | 3/1928 | Hall |
| 2,119,649 A | 6/1938 | Roosen |
| 2,135,160 A | 11/1938 | Beekhuis |
| 2,497,820 A | 2/1950 | Kielland |
| 2,686,890 A | 8/1954 | Davis |
| 3,010,347 A | 11/1961 | Kron |
| 3,016,899 A | 1/1962 | Stenvail |
| 3,017,887 A | 1/1962 | Heyer ............................ 128/348 |
| 3,055,370 A | 9/1962 | McKinney et al. |
| 3,055,371 A | 9/1962 | Kulick et al. |
| 3,115,140 A | 12/1963 | Volkman |
| 3,135,263 A | 6/1964 | Connelley, Jr. ............... 128/303 |
| 3,223,087 A | 12/1965 | Vladyka et al. |
| 3,262,452 A | 7/1966 | Hardy et al. |
| 3,273,559 A | 9/1966 | Evans |
| 3,282,152 A | 11/1966 | Myer |

(Continued)

FOREIGN PATENT DOCUMENTS

DE    3108766    9/1982

(Continued)

OTHER PUBLICATIONS

"Fathom Remote Introducer", *Image-Guided Neurologics, Inc.*, CNS Hynes Convention Center,(Oct. 30-Nov. 4, 1999), 2 pages.

(Continued)

*Primary Examiner* — Todd E Manahan
*Assistant Examiner* — Michael G Mendoza
(74) *Attorney, Agent, or Firm* — Harness, Dickey & Pierce, PLC

(57) ABSTRACT

This document discusses trajectory guides that include an instrument guide with at least one lumen angled with respect to an orthogonal or other through-axis. In one example, patterned lumens on the instrument guide provide a mirror image pattern of trajectory axes intersecting a target plane. In another example, height adjustment of the instrument guide extends these or other targeting techniques to a three-dimensional volume. This document also describes a method of manufacturing such an instrument guide, which is also applicable to manufacturing an instrument guide providing parallel lumens.

23 Claims, 20 Drawing Sheets

U.S. PATENT DOCUMENTS

| | | | |
|---|---|---|---|
| 3,402,710 A | 9/1968 | Paleschuck | |
| 3,444,861 A | 5/1969 | Schulte | |
| 3,457,922 A | 7/1969 | Ray | 128/303 |
| 3,460,537 A | 8/1969 | Zeis | 128/303 |
| 3,508,552 A | 4/1970 | Hainault | 128/303 |
| 3,672,352 A | 6/1972 | Summers | |
| 3,760,811 A | 9/1973 | Andrew | |
| 3,817,249 A | 6/1974 | Nicholson | |
| 3,893,449 A | 7/1975 | Lee et al. | |
| 3,981,079 A * | 9/1976 | Lenczycki | 433/174 |
| 4,013,080 A | 3/1977 | Froning | |
| 4,026,276 A | 5/1977 | Chubbuck | |
| 4,040,427 A | 8/1977 | Winnie | 604/180 |
| 4,131,257 A | 12/1978 | Sterling | |
| 4,230,117 A | 10/1980 | Anichkov | 128/303 B |
| 4,265,252 A | 5/1981 | Chubbuck et al. | |
| 4,312,337 A | 1/1982 | Donohue | |
| 4,318,401 A | 3/1982 | Zimmerman | |
| 4,328,813 A | 5/1982 | Ray | |
| 4,341,220 A | 7/1982 | Perry | |
| 4,345,606 A | 8/1982 | Littleford | |
| 4,350,159 A | 9/1982 | Gouda | |
| 4,355,645 A | 10/1982 | Mitani et al. | |
| 4,386,602 A | 6/1983 | Sheldon et al. | |
| 4,418,894 A | 12/1983 | Mailliet | |
| 4,448,195 A | 5/1984 | LeVeen et al. | |
| 4,463,758 A | 8/1984 | Patil et al. | |
| 4,475,550 A | 10/1984 | Bremer et al. | |
| 4,483,344 A | 11/1984 | Atkov et al. | |
| 4,571,750 A | 2/1986 | Barry | |
| 4,572,198 A | 2/1986 | Codrington | |
| 4,579,120 A | 4/1986 | MacGregor | 600/392 |
| 4,592,352 A | 6/1986 | Patil | |
| 4,598,708 A | 7/1986 | Beranek | |
| 4,608,977 A | 9/1986 | Brown | 128/303 B |
| 4,617,925 A | 10/1986 | Laitinen | 128/303 B |
| 4,618,978 A | 10/1986 | Cosman | |
| 4,629,451 A | 12/1986 | Winters et al. | 604/175 |
| 4,638,798 A | 1/1987 | Shelden et al. | 128/303 B |
| 4,660,563 A | 4/1987 | Lees | |
| 4,665,928 A | 5/1987 | Linial et al. | |
| 4,699,616 A | 10/1987 | Nowak et al. | 604/180 |
| 4,705,436 A * | 11/1987 | Robertson | 408/72 R |
| 4,706,665 A | 11/1987 | Gouda | |
| 4,733,661 A | 3/1988 | Palestrant | |
| 4,755,642 A | 7/1988 | Parks | |
| 4,791,934 A | 12/1988 | Brunnett | |
| 4,793,355 A | 12/1988 | Crum et al. | |
| 4,798,208 A | 1/1989 | Faasse, Jr. | |
| 4,805,615 A | 2/1989 | Carol | 128/303 B |
| 4,805,634 A | 2/1989 | Ullrich et al. | |
| 4,807,620 A | 2/1989 | Strul et al. | |
| 4,809,694 A | 3/1989 | Ferrara | 128/303 |
| 4,824,436 A | 4/1989 | Wolinsky | |
| 4,826,487 A | 5/1989 | Winter | 604/175 |
| 4,869,247 A | 9/1989 | Howard, III et al. | |
| 4,883,053 A | 11/1989 | Simon | 606/130 |
| 4,896,673 A | 1/1990 | Rose et al. | |
| 4,902,129 A | 2/1990 | Siegmund et al. | |
| 4,922,924 A | 5/1990 | Gambale et al. | |
| 4,955,891 A | 9/1990 | Carol | 606/130 |
| 4,957,481 A | 9/1990 | Gatenby | |
| 4,986,280 A | 1/1991 | Marcus et al. | |
| 4,986,281 A | 1/1991 | Preves et al. | |
| 4,989,608 A | 2/1991 | Ratner | |
| 4,991,579 A | 2/1991 | Allen | |
| 4,998,938 A | 3/1991 | Ghajar et al. | |
| 5,006,122 A | 4/1991 | Wyatt et al. | |
| 5,024,236 A | 6/1991 | Shapiro | |
| 5,027,818 A | 7/1991 | Bova et al. | |
| 5,030,223 A | 7/1991 | Anderson et al. | 606/130 |
| 5,050,608 A | 9/1991 | Watanabe et al. | |
| 5,052,329 A | 10/1991 | Bennett | |
| 5,054,497 A * | 10/1991 | Kapp et al. | 600/561 |
| 5,057,084 A | 10/1991 | Ensminger et al. | |
| 5,057,106 A | 10/1991 | Kasevich et al. | |
| 5,065,761 A | 11/1991 | Pell | |
| 5,078,140 A | 1/1992 | Kwoh | 128/653.1 |
| 5,078,142 A | 1/1992 | Siczek et al. | |
| 5,080,662 A | 1/1992 | Paul | 606/130 |
| 5,087,256 A | 2/1992 | Taylor et al. | |
| 5,099,846 A | 3/1992 | Hardy | |
| 5,102,402 A | 4/1992 | Dror et al. | |
| 5,116,344 A | 5/1992 | Sundqvist | |
| 5,116,345 A | 5/1992 | Jewell et al. | 606/130 |
| 5,120,322 A | 6/1992 | Davis et al. | |
| 5,125,888 A | 6/1992 | Howard et al. | |
| 5,142,930 A | 9/1992 | Allen et al. | |
| 5,143,086 A | 9/1992 | Duret et al. | |
| 5,154,179 A | 10/1992 | Ratner | |
| 5,154,723 A | 10/1992 | Kubota et al. | 606/130 |
| 5,163,430 A | 11/1992 | Carol | 128/653.1 |
| 5,166,875 A | 11/1992 | Machida | |
| 5,171,217 A | 12/1992 | March et al. | |
| 5,174,297 A | 12/1992 | Daikuzono et al. | |
| 5,186,174 A | 2/1993 | Schlondorff et al. | |
| 5,201,742 A | 4/1993 | Hasson | 606/130 |
| 5,207,223 A | 5/1993 | Adler | |
| 5,207,688 A | 5/1993 | Carol | |
| 5,211,165 A | 5/1993 | Dumoulin et al. | |
| 5,221,264 A | 6/1993 | Wilk et al. | |
| 5,222,499 A | 6/1993 | Allen et al. | |
| 5,230,338 A | 7/1993 | Allen et al. | |
| 5,230,623 A | 7/1993 | Guthrie et al. | |
| 5,242,415 A | 9/1993 | Kantrowitz et al. | |
| 5,246,448 A | 9/1993 | Chang | |
| 5,257,998 A | 11/1993 | Ota et al. | 606/130 |
| 5,263,939 A | 11/1993 | Wortrich | 604/174 |
| 5,263,956 A | 11/1993 | Nobles | 606/130 |
| 5,267,970 A | 12/1993 | Chin et al. | |
| 5,269,305 A | 12/1993 | Corol | |
| 5,279,309 A | 1/1994 | Taylor et al. | 128/782 |
| 5,279,575 A | 1/1994 | Sugarbaker | 604/174 |
| 5,280,427 A | 1/1994 | Magnusson et al. | |
| 5,290,266 A | 3/1994 | Rohling et al. | |
| 5,291,890 A | 3/1994 | Cline et al. | |
| 5,300,080 A | 4/1994 | Clayman et al. | 606/130 |
| 5,305,203 A | 4/1994 | Raab | |
| 5,306,272 A | 4/1994 | Cohen et al. | |
| 5,309,913 A | 5/1994 | Kormos et al. | |
| 5,330,485 A | 7/1994 | Clayman et al. | |
| 5,354,283 A | 10/1994 | Bark et al. | 604/180 |
| 5,361,763 A | 11/1994 | Kao et al. | |
| 5,366,446 A | 11/1994 | Tal et al. | 604/180 |
| 5,375,588 A | 12/1994 | Yoon | |
| 5,375,596 A | 12/1994 | Twiss et al. | |
| 5,380,302 A | 1/1995 | Orth | 604/523 |
| 5,383,454 A | 1/1995 | Bucholz | 128/653.1 |
| 5,387,220 A | 2/1995 | Pisharodi | |
| 5,394,457 A | 2/1995 | Leibinger et al. | |
| 5,405,330 A | 4/1995 | Zunitch et al. | |
| 5,423,832 A | 6/1995 | Gildenberg | |
| 5,423,848 A | 6/1995 | Washizuka et al. | |
| 5,445,166 A | 8/1995 | Taylor | |
| 5,452,720 A | 9/1995 | Smith et al. | |
| 5,464,446 A | 11/1995 | Dressen et al. | 607/116 |
| 5,470,307 A | 11/1995 | Lindall | |
| 5,474,564 A | 12/1995 | Clayman et al. | |
| 5,483,961 A | 1/1996 | Kelly et al. | |
| 5,494,034 A | 2/1996 | Schlondorff et al. | |
| 5,494,655 A | 2/1996 | Rocklage et al. | |
| 5,515,160 A | 5/1996 | Schulz et al. | |
| 5,517,990 A | 5/1996 | Kalfas et al. | 128/653.1 |

| | | | |
|---|---|---|---|
| 5,528,652 A | 6/1996 | Smith et al. | |
| 5,541,377 A | 7/1996 | Stuhlmacher | |
| 5,572,905 A | 11/1996 | Cook, Jr. | |
| 5,572,999 A | 11/1996 | Funda et al. | 128/653.1 |
| 5,575,798 A | 11/1996 | Koutrouvelis | |
| 5,618,288 A | 4/1997 | Calvo | |
| 5,622,170 A | 4/1997 | Schulz | |
| 5,638,819 A | 6/1997 | Manwaring et al. | |
| 5,639,276 A | 6/1997 | Weinstock et al. | |
| 5,643,286 A | 7/1997 | Warner et al. | 606/130 |
| 5,647,361 A | 7/1997 | Damadian | |
| 5,649,936 A | 7/1997 | Real | |
| 5,658,272 A | 8/1997 | Hasson | 606/1 |
| 5,662,600 A | 9/1997 | Watson et al. | |
| 5,667,514 A | 9/1997 | Heller | 606/108 |
| 5,695,501 A | 12/1997 | Carol et al. | 606/130 |
| 5,713,858 A | 2/1998 | Heruth et al. | |
| 5,755,697 A | 5/1998 | Jones et al. | |
| 5,776,064 A | 7/1998 | Kalfas et al. | |
| 5,776,143 A | 7/1998 | Adams | |
| 5,776,144 A | 7/1998 | Leysieffer et al. | 606/130 |
| 5,788,713 A | 8/1998 | Dubach et al. | |
| 5,807,033 A * | 9/1998 | Benway | 408/1 R |
| 5,809,694 A | 9/1998 | Postans et al. | |
| 5,810,712 A | 9/1998 | Dunn | 600/114 |
| 5,817,106 A | 10/1998 | Real | |
| 5,823,975 A | 10/1998 | Stark et al. | |
| 5,833,627 A | 11/1998 | Shmulewitz et al. | 600/562 |
| 5,843,150 A | 12/1998 | Dressen et al. | 607/116 |
| 5,851,183 A | 12/1998 | Bucholz | |
| 5,865,817 A | 2/1999 | Moenning et al. | |
| 5,865,842 A | 2/1999 | Knuth et al. | 607/116 |
| 5,871,445 A | 2/1999 | Bucholz | |
| 5,871,487 A | 2/1999 | Warner et al. | |
| 5,873,822 A | 2/1999 | Ferre et al. | |
| 5,891,034 A | 4/1999 | Bucholz | |
| 5,891,157 A | 4/1999 | Day et al. | 606/130 |
| 5,927,277 A | 7/1999 | Baudino et al. | 128/642 |
| 5,950,629 A | 9/1999 | Taylor et al. | |
| 5,954,687 A | 9/1999 | Baudino | 604/48 |
| 5,957,933 A | 9/1999 | Yanof et al. | |
| 5,957,934 A | 9/1999 | Rapoport | 606/130 |
| 5,964,705 A | 10/1999 | Truwit et al. | |
| 5,980,535 A | 11/1999 | Barnett et al. | |
| 5,984,930 A | 11/1999 | Maciunas et al. | 606/130 |
| 5,993,463 A * | 11/1999 | Truwit | 606/130 |
| 5,997,471 A | 12/1999 | Gumb et al. | |
| 6,006,126 A | 12/1999 | Cosman | |
| 6,018,094 A | 1/2000 | Fox | |
| 6,021,343 A | 2/2000 | Foley et al. | |
| 6,024,729 A | 2/2000 | Dehdashtian et al. | |
| 6,030,223 A | 2/2000 | Sugimori | |
| 6,039,725 A | 3/2000 | Moenning et al. | |
| 6,042,540 A | 3/2000 | Johnston et al. | |
| 6,044,304 A | 3/2000 | Baudino | 607/116 |
| 6,058,323 A | 5/2000 | Lemelson | |
| 6,071,288 A | 6/2000 | Carol et al. | 606/130 |
| 6,076,008 A | 6/2000 | Bucholz | |
| 6,079,681 A | 6/2000 | Stern et al. | |
| 6,110,182 A | 8/2000 | Mowlai-Ashtiani | 606/130 |
| 6,117,143 A | 9/2000 | Hynes et al. | 606/130 |
| 6,120,465 A | 9/2000 | Guthrie et al. | |
| 6,135,946 A | 10/2000 | Konen et al. | |
| 6,179,826 B1 | 1/2001 | Aebischer et al. | 604/522 |
| 6,195,577 B1 | 2/2001 | Truwit et al. | |
| 6,206,890 B1 | 3/2001 | Truwit | |
| 6,210,417 B1 | 4/2001 | Baudino et al. | 606/129 |
| 6,231,526 B1 | 5/2001 | Taylor et al. | |
| 6,236,875 B1 | 5/2001 | Bucholz et al. | |
| 6,238,402 B1 | 5/2001 | Sullivan, III et al. | |
| 6,254,532 B1 | 7/2001 | Paolitto et al. | 600/201 |
| 6,257,407 B1 | 7/2001 | Truwit et al. | |
| 6,261,300 B1 | 7/2001 | Carol et al. | 606/130 |
| 6,267,769 B1 | 7/2001 | Truwit | 606/130 |
| 6,267,770 B1 | 7/2001 | Truwit | |
| 6,273,896 B1 | 8/2001 | Franck et al. | |
| 6,282,437 B1 | 8/2001 | Franck et al. | |
| 6,290,644 B1 | 9/2001 | Green, II et al. | |
| 6,298,262 B1 | 10/2001 | Franck et al. | 600/426 |
| 6,315,770 B1 | 11/2001 | de la Torre et al. | |
| 6,321,104 B1 | 11/2001 | Gielen et al. | 600/378 |
| 6,327,491 B1 | 12/2001 | Franklin et al. | |
| 6,356,792 B1 | 3/2002 | Errico et al. | 607/116 |
| 6,368,329 B1 | 4/2002 | Truwit | |
| 6,400,992 B1 | 6/2002 | Borgersen et al. | |
| 6,457,963 B1 | 10/2002 | Tawara et al. | |
| 6,482,182 B1 | 11/2002 | Carroll et al. | 604/174 |
| 6,488,620 B1 | 12/2002 | Segermark et al. | |
| 6,491,699 B1 | 12/2002 | Henderson et al. | |
| 6,529,765 B1 * | 3/2003 | Franck et al. | 600/427 |
| 6,537,232 B1 | 3/2003 | Kucharczyk et al. | |
| 6,546,277 B1 | 4/2003 | Franck et al. | |
| 6,546,279 B1 | 4/2003 | Bova et al. | |
| 6,547,795 B2 | 4/2003 | Schneiderman | |
| 6,556,857 B1 | 4/2003 | Estes et al. | |
| 6,609,020 B2 | 8/2003 | Gill | |
| 6,610,100 B2 | 8/2003 | Phelps et al. | |
| 6,632,184 B1 | 10/2003 | Truwit | |
| 6,655,014 B1 | 12/2003 | Babini | |
| 6,662,035 B2 | 12/2003 | Sochor | 600/378 |
| 6,676,669 B2 | 1/2004 | Charles et al. | |
| 6,706,050 B1 | 3/2004 | Giannadakis | |
| 6,726,678 B1 | 4/2004 | Nelson et al. | |
| 6,746,471 B2 | 6/2004 | Mortier et al. | |
| 6,752,812 B1 | 6/2004 | Truwit | |
| 6,765,122 B1 | 7/2004 | Stout | |
| 6,773,443 B2 | 8/2004 | Truwit et al. | |
| 6,782,288 B2 | 8/2004 | Truwit et al. | |
| 6,802,323 B1 | 10/2004 | Truwit et al. | |
| 6,902,569 B2 | 6/2005 | Parmer et al. | |
| 6,913,478 B2 | 7/2005 | Lamirey | |
| 6,944,895 B2 | 9/2005 | Truwit | |
| 6,960,216 B2 * | 11/2005 | Kolb et al. | 606/96 |
| 7,479,146 B2 | 1/2009 | Malinowski | |
| 2001/0014771 A1 | 8/2001 | Truwit et al. | |
| 2001/0027271 A1 | 10/2001 | Franck et al. | 600/426 |
| 2001/0037524 A1 | 11/2001 | Truwit | |
| 2002/0010479 A1 | 1/2002 | Skakoon et al. | |
| 2002/0019641 A1 | 2/2002 | Truwit | |
| 2002/0022847 A1 | 2/2002 | Ray et al. | |
| 2002/0052610 A1 | 5/2002 | Skakoon et al. | |
| 2002/0077646 A1 | 6/2002 | Truwit et al. | |
| 2002/0156372 A1 | 10/2002 | Skakoon et al. | |
| 2003/0079287 A1 | 5/2003 | Truwit | |
| 2003/0187351 A1 | 10/2003 | Franck et al. | |
| 2003/0208122 A1 | 11/2003 | Melkent et al. | |
| 2004/0059260 A1 | 3/2004 | Truwit | |
| 2004/0176750 A1 | 9/2004 | Nelson et al. | |
| 2004/0243147 A1 | 12/2004 | Lipow | |
| 2004/0255991 A1 | 12/2004 | Truwit et al. | |
| 2004/0260323 A1 | 12/2004 | Truwit et al. | |
| 2004/0267284 A1 | 12/2004 | Parmer et al. | |
| 2006/0192319 A1 | 8/2006 | Solar | |
| 2006/0195119 A1 | 8/2006 | Mazzocchi et al. | |
| 2007/0250078 A1 | 10/2007 | Stuart | |
| 2007/0299427 A1 | 12/2007 | Yeung et al. | |
| 2008/0004632 A1 | 1/2008 | Sutherland et al. | |

FOREIGN PATENT DOCUMENTS

| | | |
|---|---|---|
| DE | 3937052 | 5/1990 |
| DE | 29612100 | 9/1996 |
| DE | 19726141 | 1/1999 |
| DE | 19826078 | 8/1999 |
| DE | 19808220 | 9/1999 |

| | | |
|---|---|---|
| DE | 19820808 | 11/1999 |
| EP | 0386936 | 9/1990 |
| EP | 0427358 | 5/1991 |
| EP | 0609085 | 8/1994 |
| EP | 0724865 | 8/1996 |
| EP | 0832611 | 4/1998 |
| EP | 0904741 | 3/1999 |
| GB | 2237993 | 5/1991 |
| GB | 2329473 | 3/1999 |
| GB | 2346573 | 8/2000 |
| GB | 2346573 A * | 8/2000 |
| WO | WO-8809151 | 12/1988 |
| WO | WO-95/22297 | 8/1995 |
| WO | WO-96/10368 | 4/1996 |
| WO | WO-9633766 | 10/1996 |
| WO | WO-9703609 | 2/1997 |
| WO | WO-97/21380 | 6/1997 |
| WO | WO-9742870 | 11/1997 |
| WO | WO-98/17191 | 4/1998 |
| WO | WO-98/25535 | 6/1998 |
| WO | WO-9851229 | 11/1998 |
| WO | WO-00/01316 | 1/2000 |
| WO | WO-0018306 | 4/2000 |
| WO | WO-0124709 | 4/2001 |
| WO | WO-01/49197 A1 | 7/2001 |
| WO | WO-0176498 A2 | 10/2001 |
| WO | WO-0176498 A3 | 10/2001 |
| WO | WO-2004026161 A2 | 4/2004 |

OTHER PUBLICATIONS

Franck, Joel, et al., "microTargetingR Platform System incorprating StarFixTM guidance", microTargeting, 44.

Grady, M., et al., "Nonlinear Magnetic Stereotaxis: Three-Dimensional, in vivo Remote Magnetic Manipulation of a Small Object in Canine Brain", Medical Physics, 17 (3), (May/Jun. 1990), pp.405-415.

Hata, N., et al., "Needle Insertion Manipulator for CT—and MR-Guided Stereotactic Neurosurgery", Interventional MR: Techniques and Clinical Experience, St. Louis : London : Mosby ; Martin Dunitz, F. Jolesz and I. Young, eds., (1998), 99-106.

Hirschberg, H., et al., "Image-guided neurosurgery—MR compatible stereotactic equipment", http:www.medinnova. no/English/P51466ster.html, (Mar. 29, 2001), 1 p. (viewed web site on Mar. 29, 2001).

Leggett, W. B., et al., "Surgical Technology—The Viewing Wand: A New System for Three-Dimensional Computed Tomography-Correlated Intraoperative Localization", Current Surgery, (Dec. 1991), 674-678.

Oliver, L., "Cup-And-Ball Chemopallidectomy Apparatus", (1958),p. 401.

Sandeman, D. S., et al., "Advances in image-directed neurosurgery: Preliminary experience with the ISG Viewing Wand compared with the Leksell G frame", British Journal of Neurosurgery. 8, (199),pp. 529-544.

Yeh, H.-S., et al., "Implantation of intracerebral depth electrodes for monitoring seizures using the Pelorus stereotactic system guided by magnetic resonance imaging", J. Neurosurg., 78, (1993), pp. 138-141.

Zinreich, S. J., et al., "Frameless Stereotaxic Integration of CT Imaging Data: Accuracy and Initial Applications", Radiology, 188 (3), (1993), pp. 735-742.

"Cross-Hairs Kit", Elekta Instruction for Use Brochure, pp. 1-5.

"CRWTM—Tyco Healthcare Radionics", Tyco Product Brochure, pp. 1-7.

"Leksell Sterotatic System", Elekta Product Brochure, pp. 1-6.

International Search Report and Written Opinion for PCT/US05/43651 mailed May 8, 2008.

Ritter, R., et al., "Stereotaxie Magnetique: Deplacement D'Implants dans le Cerveau, Assistes par Ordinateur et Guides par Imagerie", Innovation et Technologie en Biologie et Medecine, 13, (1992), 437-449.

Supplementary European Search Report mailed Oct. 26, 2009 for EP05852969 filed Dec. 6, 2005 claiming benefit of U.S. Appl. No. 11/005,907 filed Dec. 5, 2004.

"Inomed Competence in Neurophysiologic Monitoring", http://www.inomed.com/english/index.htm, (observed Mar. 23, 2004), 2 pgs.

"MicroTargeting® Precision Guidance Using Microelectrode Recording", (Aug. 15, 2003), 5 pgs.

"Possible Existence of Common Internalization Mechanisms among Arginine-rich Peptides", Suzuki, T. et al., Journal of Biological Chemistry, vol. 277, No. 4 (2002) pp. 2437-2443.

Allison, S., et al., "Microchannel Plate Intensifier Response in Traverse Magnetic Field", Electronic Letters, 26, (Jun. 7, 1990), 770-771.

Drake, J. M., et al., "ISG Viewing Wand System", Neurosurgery, 34 (6), (Jun. 1994), pp. 1094-1097.

Dyer, P. V., et al., "The ISG Viewing Wand: an application to atlanto-axial cervical surgery using the Le Fort I maxillary osteotomy", British Journal of Oral and Maxillofacial Surgery, 33, (1995), pp. 370-374.

Franck, Joel, et al., "microTargeting® Platform incorporating StarFix™ guidance", microTargeting, 3 pgs.

Gehring, W. J., "Homeodomain Proteins", Annu. Rev. Biochem., vol. 63 (1997) pp. 487-526.

Gillies, G., et al., "Magnetic Manipulation Instrumentation for Medical Physics Research", Review of Scientific Instruments, 65 (3), Review Article, (Mar. 1994), 533-562.

Grady, M. S., "Magnetic Stereotaxis System for Neurosurgical Procedures", Proceedings of the 37th International Instrumentation Symposium, (May 5-9, 1991), pp. 665-675.

Grady, M. S., et al., "Initial Experimental Results of a New Stereotaxic Hyperthermia System", American College of Surgeons, Surgical Forum, vol. XXXIX, Neurological Surgery (1988), pp. 507-509.

Grady, M. S., et al., "Magnetic Stereotaxis: A Technique to Deliver Stereotactic Hyperthermia", Neurosurgery, 27 (6), (1990), pp. 1010-1016.

Grady, M. S., et al., "Preliminary experimental investigation of in vivo magnetic manipulation: Results and potential application in hyperthermia", Medical Physics, 16 (2), (Mar./Apr. 1989), pp. 263-272.

Hirschberg, Henry, et al., "Image-guided neurosurgery", stereotactic equipment for MR imaging, http://www.medinnova.no/English/P51466ster.html, (Observed Mar. 8, 2002), 1 page.

Howard III, M. A., et al., "Magnetic Neurosurgery: Image-Guided Remote-Controlled Movement of Neurosurgical Implants", Clinical Neurosurgery, (1995), pp. 382-391.

Howard III, M. A., et al., "Review of Magnetic Neurosurgery Research", Journal of Image Guided Surgery, 1 (6), (1995), pp. 295-299.

Howard, M. A., et al., "Magnetic Movement of a Brain Thermoceptor", Neurosurgery, 24 (3) (Mar. 1989), pp. 444-448.

Howard, M. A., et al., "Magnetic Neurosurgery", Proceedings of the Meeting of the American Society for Stereotactic and Functional Neurosurgery, (Mar. 8-11, 1995), pp. 102-107.

Lawson, M. A., et al., "Near Real-Time Bi-planar Fluoroscopic Tracking System for the Video Tumor Fighter", SPIE, vol. 1445 Image Processing, (1991), pp. 265-275.

Malison, R. T., et al., "Computer-Assisted Coregistration of Multislice SPECT and MR Brain Images by Fixed External Fiducials", Journal of Computer Assisted Tomography, 17 (6) (1993) pp. 952-960.

Mannervik, M., "Target genes of homeodomain proteins", BioEssays vol. 21.4 (Apr. 1999) pp. 267-270.

McNeil, R. G., et al., "Characteristics of an Improved Magnetic-Implant Guidance System", IEEE Transactions on Biomedical Engineering, 42 (8), (Aug. 1995), pp. 802-808.

McNeil, R. G., et al., "Functional Design Features and Initial Performance Characteristics of a Magnetic-Implant Guidance System for Stereotactic Neurosurgery", IEEE Transactions on Biomedical Engineering, 42 (8), pp. 793-801.

Meeker, D., et al., "Optimal Realization of Arbitrary Forces in a Magnetic Stereotaxis System," IEEE Transactions on Magnetics, 32 (2), (Mar. 1996), 320-328.

Molloy, J. A., et al., "Experimental Determination of the Force Required for Insertion of a Thermoseed Into Deep Brain Tissues", *Annals of Biomedical Engineering*, 18 (3), (1990), pp. 299-313.

Molloy, J. A., et al., "Thermodynamics of movable inductively heated seeds for the treatment of brain tumors", *Medical Physics*, 18 (4), (Jul./Aug. 1991), pp. 794-803.

Patikoglou, G. et al., "Eukaryotic Transcription Factor-DNA Complexes", Annual Review of Biophysics and Biomolecular Structure vol. 26 (1997) pp. 289-325.

Quate, E., et al., "Goniometric Motion Controller for the Superconducting Coil in a Magnetic Stereotaxis System", IEEE Transactions on Biomedical Engineering, 38 (9), (Sep. 1991), 899-905.

Ramos, P. A., et al., "Electro-optic imaging chain for a biplanar fluoroscope for neurosurgery: magnetic field sensitivity and contrast measurements", *Optical Engineering*, 32 (7), (Jul. 1993), pp. 1644-1656.

Ramos, P. A., et al., "Low-dose, magnetic field-immune, bi-planar fluoroscopy for neurosurgery", *SPIE Medical Imaging V: Image Physics*, vol. 1443, (1991), pp. 160-170.

Ramos, P. A., et al., "Microchannel Plate Image Intensifier Electron Dynamics in Magnetic Field", *Electronics Letters*, 27 (18), (Aug. 29, 1991), pp. 1636-1638.

Ritter, R. C., et al., "Magnetic Stereotaxis: An Application of Magnetic Control Technology to the Needs of Clinical Medicine", *Proc. Of the MAG '95 Industrial Conf. And Exhibition, Technomic Pub. Co., Lancaster, Pa., Allaire, P., ed.*, (1995), pp. 186-193.

Ritter, R. C., et al., "Magnetic Stereotaxis: Computer-Assisted Image-Guided Remote Movement of Implants in the Brain", *Computer-Integrated Surgery: Technology and Clinical Applications*,MIT Press, (1996), pp. 363-369.

Stein, S. et al., "Checklist: Vertebrate homeobox genes", Mechanisms of Development, vol. 55, No. 1 (Mar. 1996) pp. 91-108.

Szikora, I., et al., "Endovascular Treatment of Experimental Aneurysms with Liquid Polymers: The Protective Potential of Stents", *Neurosurgery*, 38, (Feb. 1996), pp. 339-347.

Vollmer, J. et al., "Homeobox Genes in the Developing Mouse Brain", Journal of Neurochemistry, vol. 71, No. 1 (Jul. 1998) pp. 1-19.

Wolberger, C., "Homeodomain Interactions", Current Opinion in Structural Biology vol. 6, No. 1 (Feb. 1996) pp. 62-68.

* cited by examiner

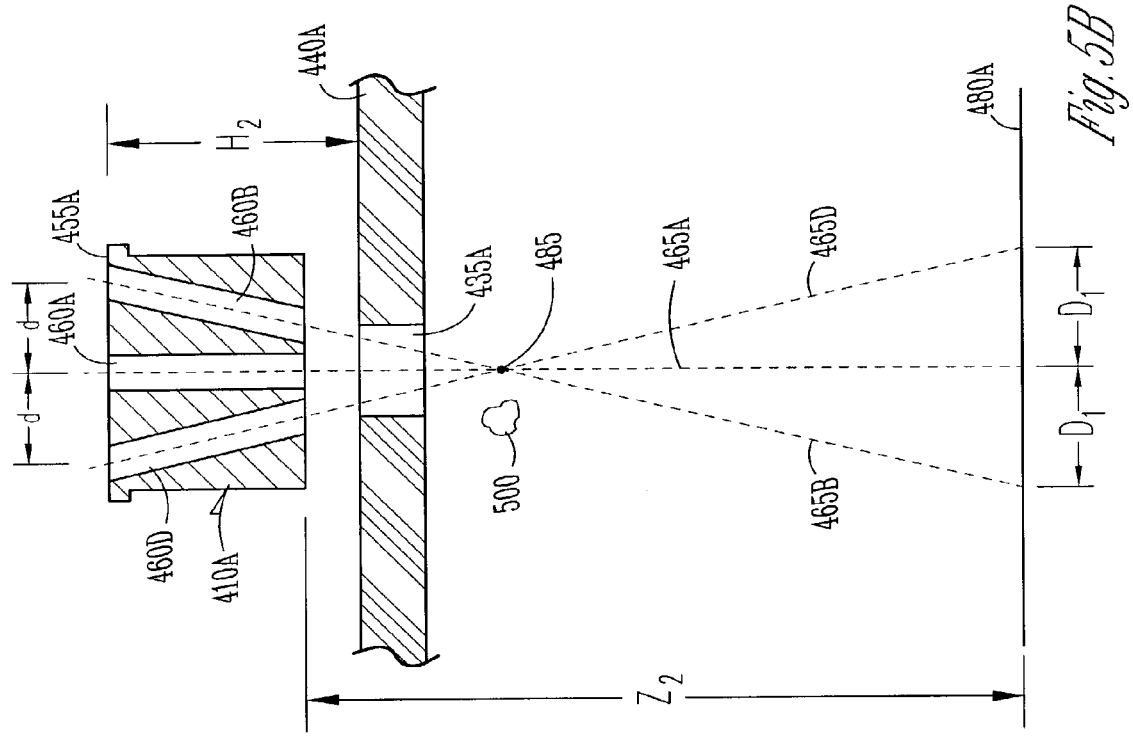
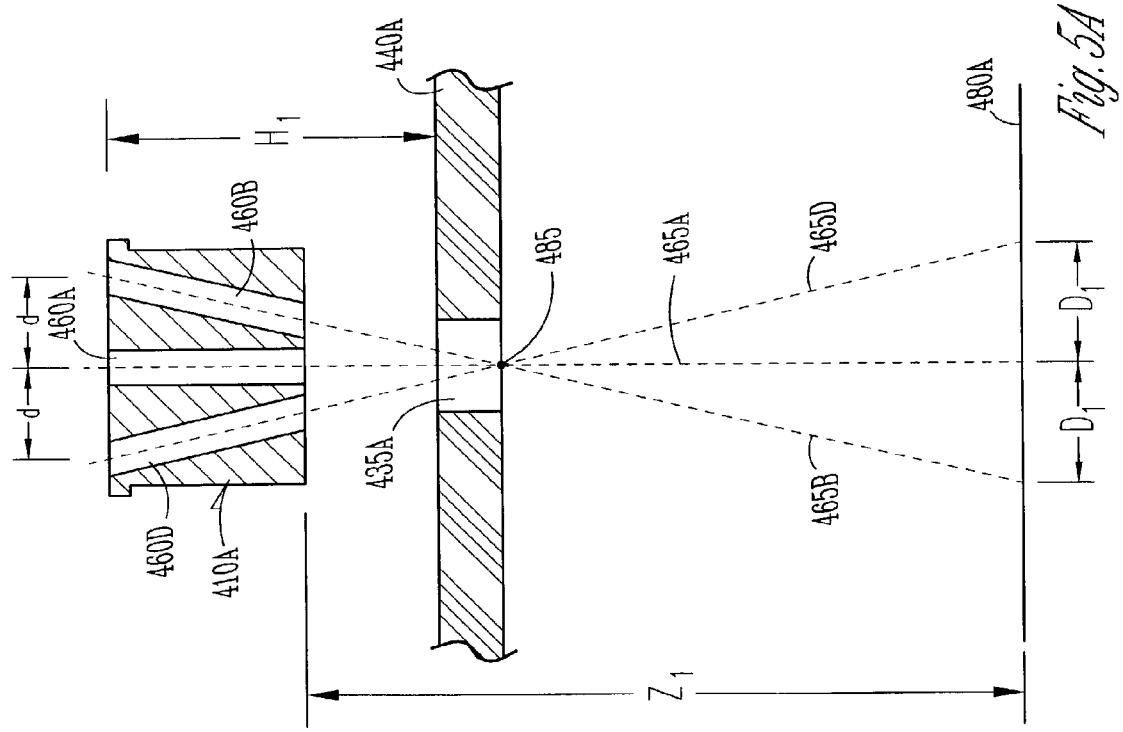

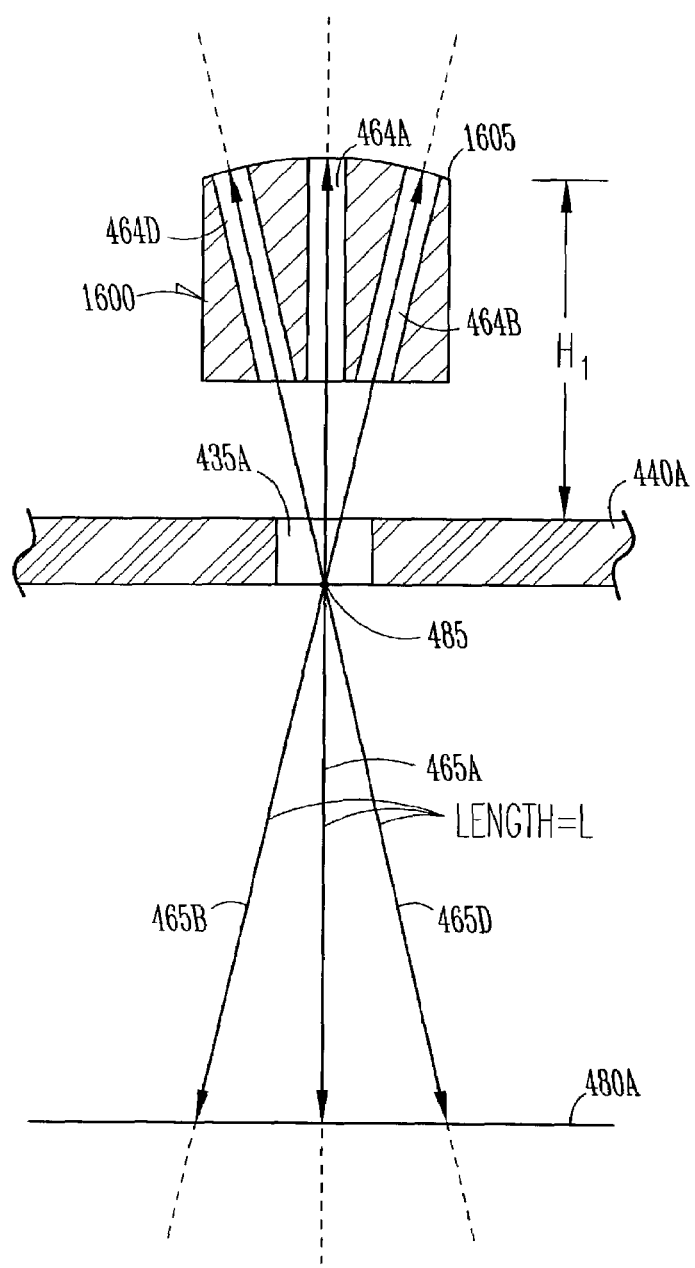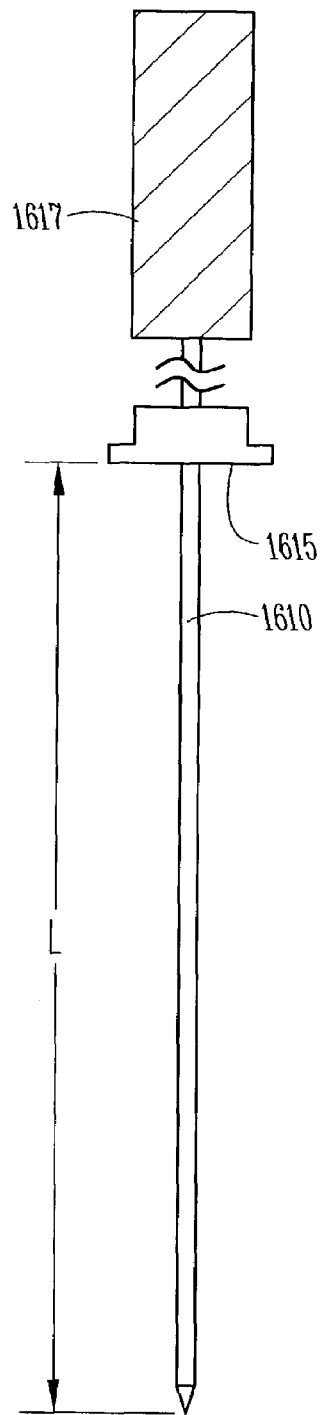
Fig. 16A
Fig. 16B

TRAJECTORY GUIDE WITH ANGLED OR PATTERNED LUMENS OR HEIGHT ADJUSTMENT

FIELD OF THE INVENTION

This document relates generally to trajectory guides, and more specifically, but not by way of limitation, to a trajectory guide with at least one angled lumen or with patterned lumens.

BACKGROUND

Neurosurgery sometimes involves inserting an instrument through a burr hole or other entry portal into a subject's brain toward a target region of the brain. Because of the precision needed to reach the target, while avoiding nearby structures that are often critical to brain function, stereotactic instrument guidance is sometimes provided. In one such technique, a stereotactic headframe is mounted about the patient's skull. A trajectory guide is mounted to the headframe to provide an instrument-guiding trajectory through the burr hole and aimed toward the target. In another technique (sometimes referred to as "frameless stereotaxy"), a trajectory guide is mounted directly to the skull in or about the burr hole. The skull-mounted trajectory guide also provides an instrument-guiding trajectory through the burr hole and aimed toward the target. In either technique, an image-guided workstation may be used to provide navigational guidance to the neurosurgeon, such as by displaying preoperative images of the subject to assist the neurosurgeon in planning or performing the procedure.

Among other things, the present inventors have recognized that the limited diameter of the burr hole limits the size and location of the target area that can be accessed via the burr hole. The present inventors have also recognized an unmet need for reducing trauma to the brain. For these and other reasons, which will become apparent upon reading the following detailed description and viewing the drawings that form a part thereof, the present inventors have recognized an unmet need for trajectory guide systems, devices, and methods that provide improved access and/or reduced trauma.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIGS. 5A, 5B, 5C, 5D, 5E, and 5F are cross-sectional schematic diagrams illustrating various operative embodiments of angled-lumen instrument guides.

FIG. 16A is a cross-sectional schematic diagram illustrating generally one example of an instrument guide having a top surface that is curved, faceted, or otherwise designed to obtain a fixed length L between a top surface and a range plane.

FIG. 16B is a side view schematic diagram illustrating generally one example of an instrument having a length L and capable of being inserted through an instrument guide lumen.

DETAILED DESCRIPTION

In the following detailed description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

Figure 1:
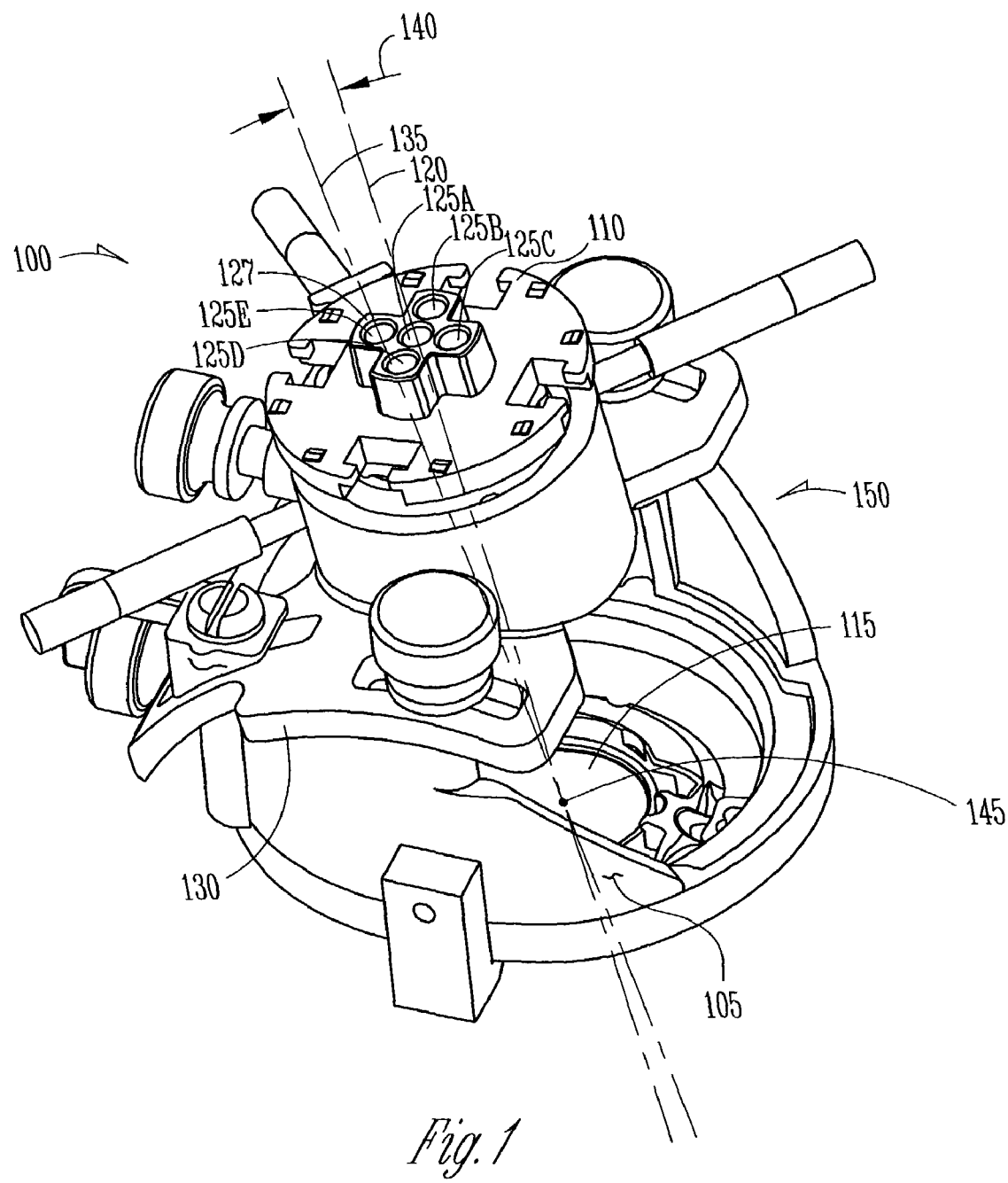
FIG. 1 is a schematic diagram illustrating generally, by way of example, but not by way of limitation, a perspective view of one embodiment of an instrument-guiding apparatus, referred to herein as a "trajectory guide" assembly.

FIG. 1 is a schematic diagram illustrating generally, by way of example, but not by way of limitation, a perspective view of one embodiment of an instrument-guiding apparatus, referred to herein as a "trajectory guide" assembly 100. Certain portions of this example of trajectory guide 100 are described in more detail in Skakoon et al. U.S. patent application Ser. No. 09/828,451, entitled "DEEP ORGAN ACCESS DEVICE AND METHOD," which was filed on Apr. 6, 2001, the disclosure of which is incorporated herein by reference in its entirety, including its description of a trajectory guide that is, among other things, rotatable around an axis extending orthogonally from the skull and tiltable at an angle from said axis.

In FIG. 1, trajectory guide 100 includes, among other things, a base 105 and an instrument guide 110. In this example, the base 105 is sized and shaped for securing in or about an entry portal 115 in a human, animal, or other subject that includes a desired target within the subject beyond the entry portal 115. In one example, the entry portal 115 is an approximately circular burr hole that has been drilled or otherwise formed in the subject's skull for accessing an underlying target region within the subject's brain. In one example, the base 105 is mounted to the skull around the burr hole entry portal 115 using bone screws. The circular burr hole or other entry portal 115 can be conceptualized as defining an entry plane, e.g., tangential to the skull's outer surface, tangential to its inner surface, or tangential to a midportion therebetween.

The instrument guide 110 can be conceptualized as including a through axis 120. In this particular example, axis 120 extends substantially orthogonally through the instrument guide 110, as illustrated in FIG. 1, such that it is directed at a center point of the entry portal 115 about which the base 105 is disposed. In this example, the instrument guide 110 is coupled to the base 105 such that the instrument guide 110 is capable of being adjustably oriented with respect to the base 105 to adjustably direct the axis 120 to extend through the entry portal 120 toward the desired target. In the illustrative example of FIG. 1, a portion of the base 105 rotates concentrically about the entry portal 115 and a sliding saddle 130, carrying the instrument guide 110, tilts along an arc portion of the base 105 to adjust the angle at which the axis 120 intersects the tangential entry plane defined by the entry portal 115.

At least one lumen 125 extends through the instrument guide 110 for providing an instrument-guiding trajectory path therethrough. As an illustrative example, but not by way of limitation, FIG. 1 depicts five lumens 125A-E. The illustrative lumens 125A-E include a center lumen 125A, and four offset lumens 125B-E displaced from the center lumen 125A by at least one predetermined center-to-center distance. In the illustrative example of FIG. 1, the offset lumens 125B-E are arranged about the center lumen 125A (e.g., along the substantially planar or other top surface of the instrument guide 110) analogous to a North-South-East-West distribution pattern.

In the illustrative example of FIG. 1, the axis 120 extends coaxially through the center lumen 120A, and extends substantially orthogonally or normal to the planar or other proximal outer surface 127 of the instrument guide 110. In this example, the instrument guide 110 includes at least one lumen (such as lumen 125E) defining a corresponding axis extending coaxially therethrough (such as a corresponding axis 135) at a predetermined angle (such as an angle 140) with the axis 120. Therefore, in this example, the nonparallel and intersecting axes 120 and 135 define a plane in which the angle 140 lies. Moreover, in this example, the axes 120 and 135 intersect at a point 145 located at the entry portal, or beyond the entry portal, i.e., further within the subject. However, this is not a requirement; in an alternative example, the intersection point 145 is located above the entry portal 115, i.e., outside of the subject. (In yet another alternative example, nonparallel axes 120 and 135 do not intersect at all, as discussed below). In a further example, as discussed further below, trajectory guide 100 provides an adjustable height of the instrument guide 110 above the entry portal 115. By adjusting the height of the instrument guide 110 above the entry portal 115, a depth (at or beneath the entry portal 115) or height (above the entry portal 115) of the intersection point 145 (if any) can thereby be adjusted. Although the instrument guide 110 is illustrated in FIG. 1 as including five lumens 125, it is understood that instrument guide 110 could include a fewer or greater number of lumens 125. In addition, such lumens 125 can be configured in a different pattern than illustrated in FIG. 1. Moreover, in FIG. 1, one or more of the other offset lumens 125B-E may also be configured to define a corresponding coaxially-extending axis at a predetermined angle with axis 120 (which angle may be the same or a different predetermined value than that of the illustrated angle 140). In one example, the offset lumens 125B-E are constructed with respective coaxially-extending axes at like predetermined angles with axis 120, such that these axes all intersect at a single point 145 (such as a single cortical entry point that is at or near the surface of the subject's brain substantially adjacent to the entry portal 115; this reduces cortical damage that would otherwise result from multiple parallel tracks extending into the subject's brain). In one example, the center lumen 125A is omitted, such that the axis 120 extends substantially orthogonally through instrument guide 110, but does not extend coaxially through the center lumen 125A. In this example, the instrument guide 110 includes at least one lumen defining a coaxial axis that is angled with respect to the axis 120, as described above.

Figure 2:
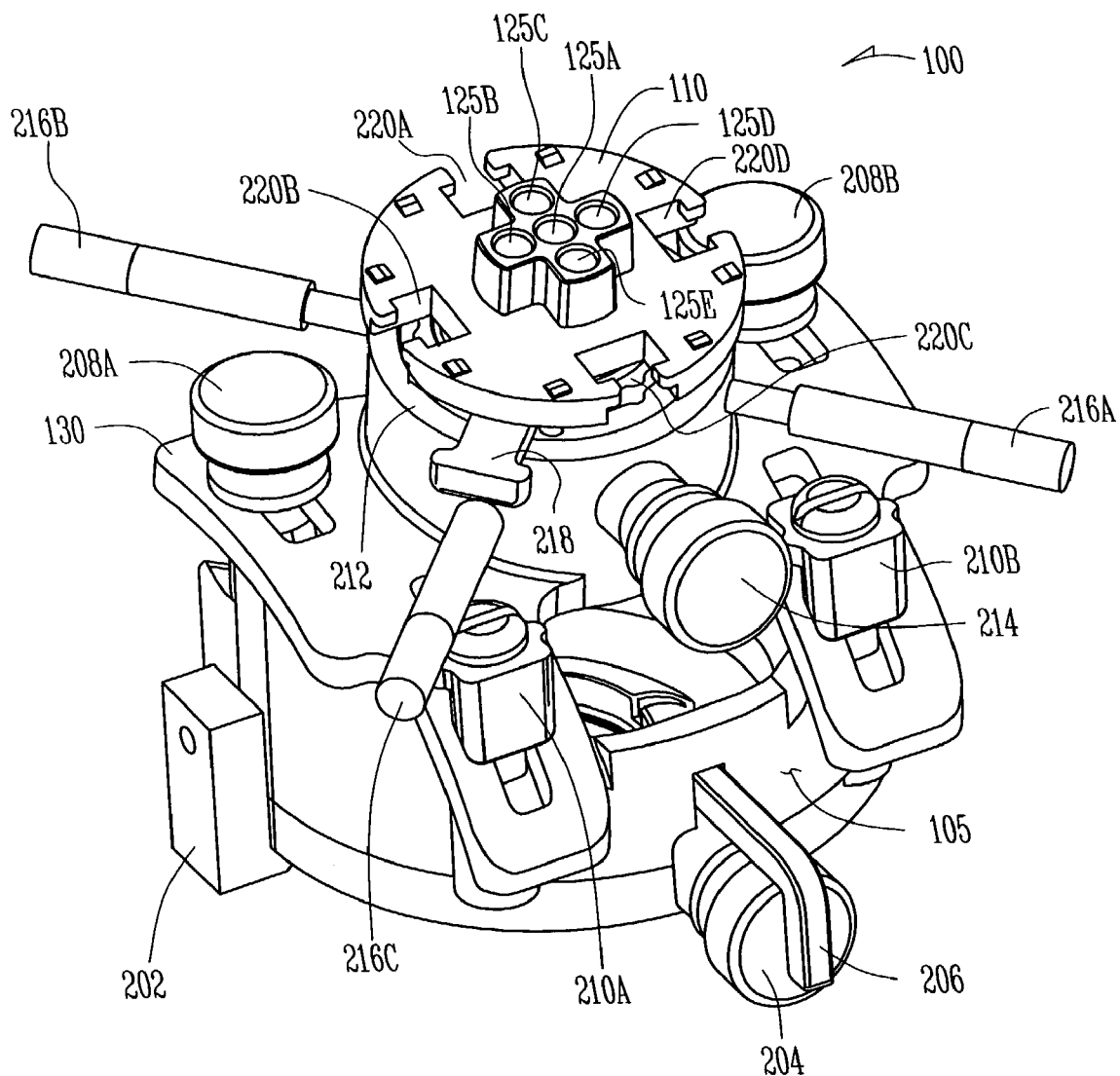
FIG. 2 is a perspective view further illustrating, by way of example, but not by way of limitation, certain portions of an exemplary trajectory guide assembly.
Figure 3:
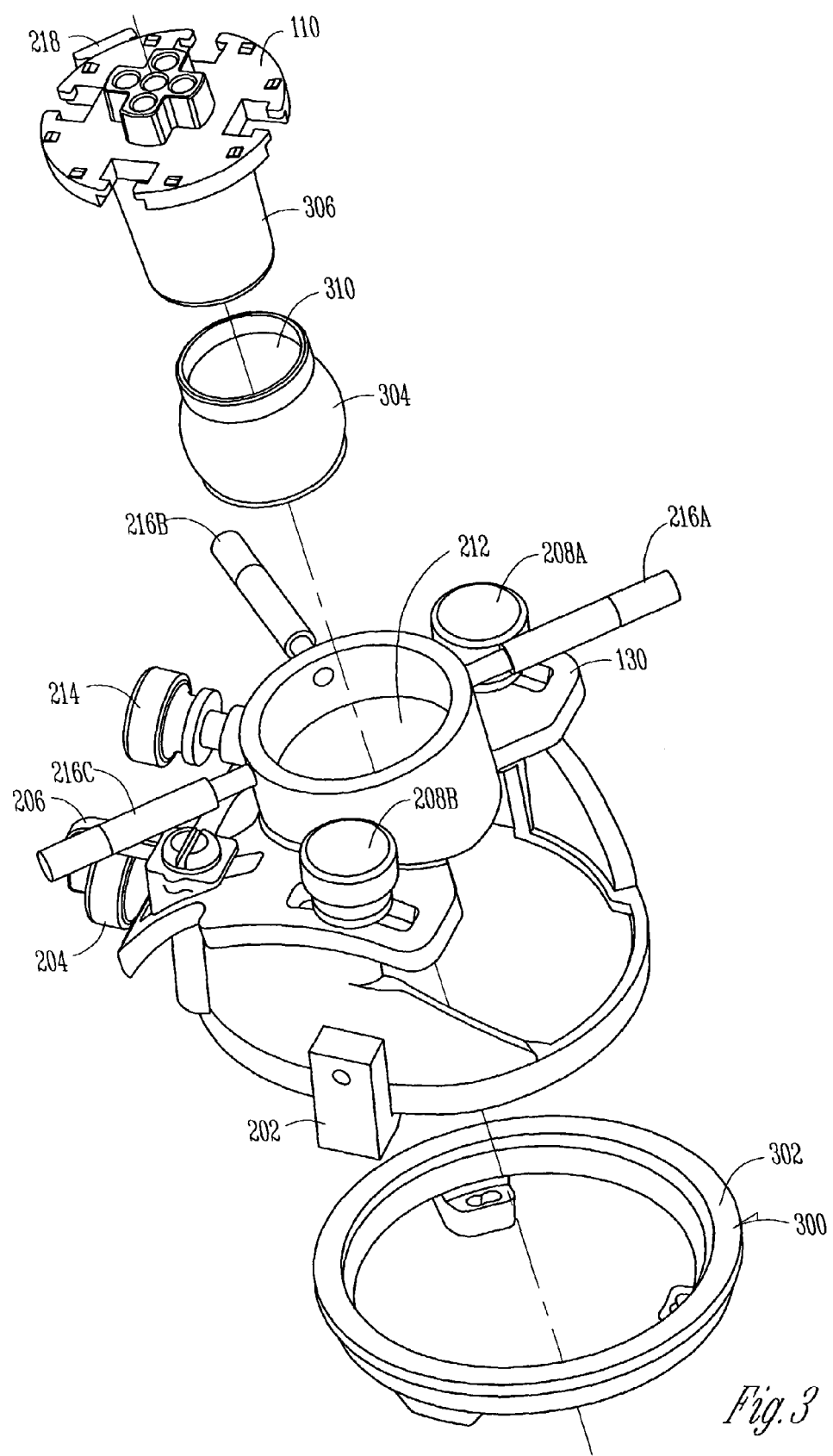
FIG. 3 is an exploded view further illustrating, by way of example, but not by way of limitation, certain portions of an exemplary trajectory guide assembly.

FIGS. 2 and 3 are respective perspective and exploded views further illustrating, by way of example, but not by way of limitation, certain portions of the exemplary trajectory guide assembly 100. In this illustrative example, a tower-like portion of the base 105 snaps onto and rotates upon a ring-like or other platform 300, such as by using one or more snap-fitting side blocks 202. The side blocks 202 provide added stability. This reduces or avoids side-to-side rocking of the tower-like portion of the base 105 riding on a platform ring surface 302. The curved saddle 130 is coupled to and seated on a curved arc portion of tower-like portion of the base 105, such as by using at least one semispheric arcuate sliding joint or the like, as illustrated. The curved portions of the saddle 130 and the tower-like portion of the base 105 can be tilted with respect to each other to alter a trajectory angle of an instrument being introduced through the instrument guide 110. The saddle 130 can be secured to fix this aspect of the trajectory angle of the instrument into the entry plane.

In this example, an affixation mechanism, such as a thumbscrew 204, passes through an opening in the tower-like portion of the base 105 and engages a portion of the platform 300 to prevent further rotation of the tower-like portion of the base 105 with respect to the platform 300 once a desired rotational position has been obtained. In this example, a capturing device, such as an L-shaped arm 206, retains the thumbscrew 204 together with the base 105.

Another affixation mechanism, such as a thumbscrew 208A-B, passes through a slotted opening (tilt slot) in the saddle 130 and engages a portion of the base 105 to prevent further riding of the curved portion of the saddle 130 along the curved portion of the base 105 once a desired trajectory angle has been obtained. This example also includes attachment fasteners 210A-B passing through corresponding slots in the saddle 130 for additionally securing the saddle 130 to the base 105. In this illustrative example, the attachment fasteners 210A-B include screws passing through respective retainer brackets, each of which includes a curved surface conforming to a curved surface of the saddle 130.

Also in this example, an interior portion of a socket or other receptacle 212 on the saddle 130 provides a socket portion of a ball-and-socket joint. An affixation mechanism, such as a thumbscrew 214, passes through a threaded opening in the socket 212 to secure the position of a ball 304 housed therein. The socket 212 also includes fine-tuning thumbscrews 216A-C, which pass through threaded openings in the socket 212 for further adjusting the exact position of the ball 304 within the socket 212. The socket 212 further carries the instrument guide 110. In this example, the instrument guide 110 includes a tapered barrel sleeve 306 that is releasably coupled, such as by release tab 218 and associated structure(s), within a cylindrical opening 310 through the ball 304.

However, in an alternative example, the ball 304 is omitted, and the barrel sleeve 306 is sized and shaped to be received directly within the collar of the receptacle 212. In one such example, the fine-tuning thumbscrews 216A-C are also omitted. In another such example, the fine-tuning thumbscrews 216A-C are replaced by a single thumbscrew, e.g., the thumbscrew 216A. In a further example, the barrel sleeve 306 includes threads mating to threads on an interior portion of the receptacle 212. This implements an adjustable coupling device that adjustably couples the instrument guide 110 to the base 105. For example, this allows adjustment of the height of the instrument guide 110 above the entry portal 115 by screwing the barrel sleeve 306 into the threaded receptacle 212 by an appropriate amount. In another example, the height is adjusted by inserting a non-threaded barrel sleeve 306 into a non-threaded receptacle 212 by the desired amount. Then, barrel sleeve 306 is locked down, such as by tightening the thumbscrew 216A, or by using any other suitable fixation technique.

In the example of FIG. 3, to release the instrument guide 110 from the ball 304, the tab 218 is pressed inward toward the sleeve 306. This forces or wedges a portion of the release tab 218 against a top portion of the ball 304 and aids in releasing the instrument guide 110 from the ball 304. The top portion of the instrument guide 110 provides at least one instrument-guiding lumen 125, such as discussed above with respect to FIG. 1. In this example, the instrument guide 110 also includes T-shaped receptacles or recesses 220A-D for receiving further attachable equipment. In one embodiment, the instrument guide 110 (or an apparatus coupled thereto) includes one or more fiducial markers (e.g., LEDs, reflectors, microcoils, MR-visible components, or other locators), such as for assisting the user in obtaining the desired trajectory alignment in a frameless surgical navigation system and/or in an MRI environment.

In the examples of FIGS. 1-3, a portion 150 of the tower-like base 105 is left open, allowing viewing of the entry portal 115. Moreover, this advantageously permits viewing and/or access of any instruments being inserted through the entry portal 115. In one example, as illustrated in FIGS. 1-3, the open portion 150 is facilitated by restricting the saddle movement of saddle 130 such that, when the base 105 is fixed with respect to the platform ring 302, the saddle movement adjusts the angle between axis 120 and an axis normal to the entry portal 115 in a single direction from the axis normal to the entry portal 115, rather than in two directions with respect thereto. However, this represents merely one technique of leaving the entry portal 115 viewable and/or accessible; a cutout portion of the instrument guide 110, or any other viewing and/or access technique may alternatively be used.

Figure 4A:
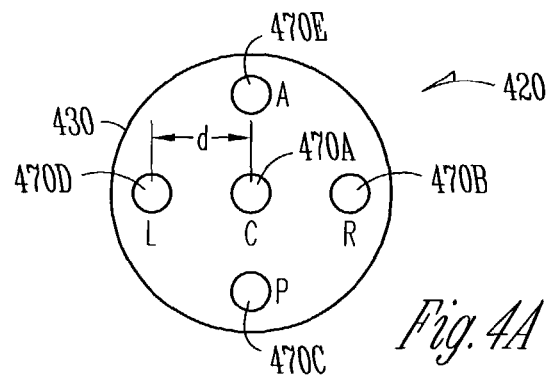
FIG. 4A is a conceptualized schematic diagram illustrating a top view of an instrument guide having one or more parallel lumens extending orthogonally through the instrument guide.
Figure 4B:
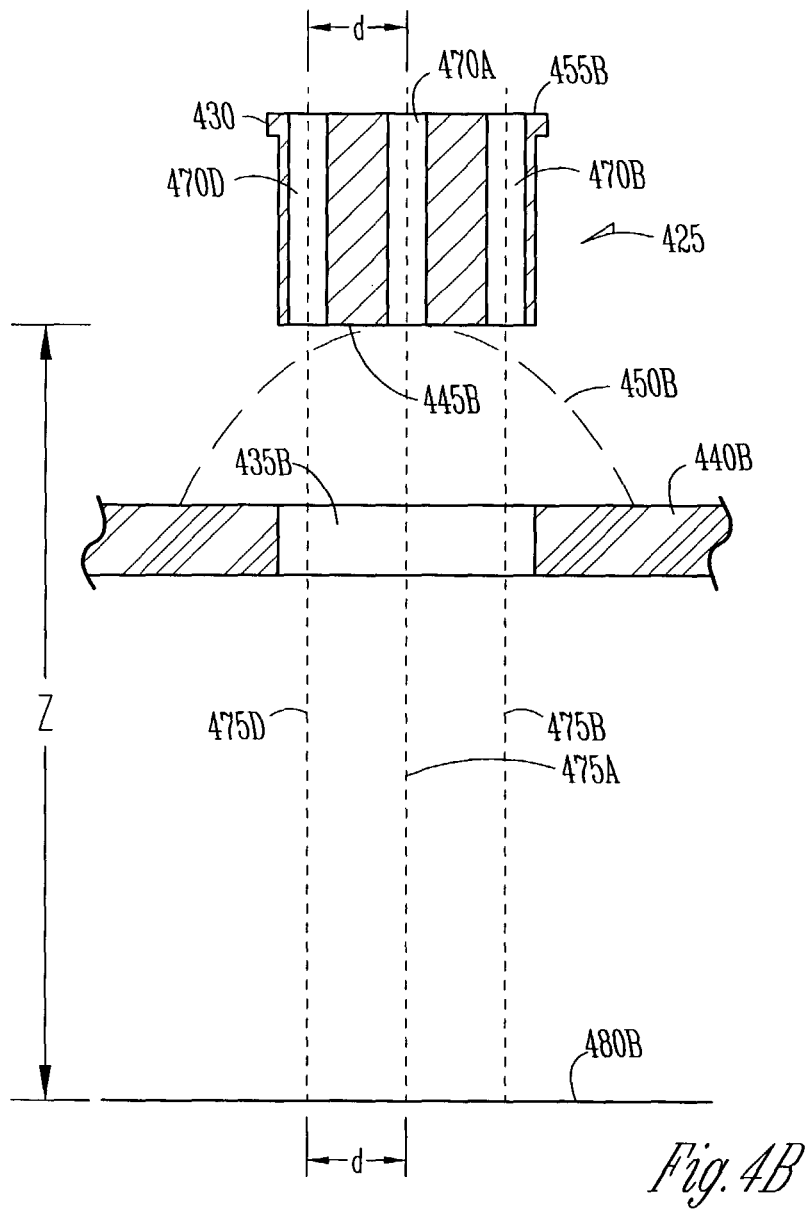
FIG. 4B is a conceptualized schematic diagram illustrating a cross-sectional side view of an instrument guide having one or more parallel lumens extending orthogonally through the instrument guide.
Figure 4C:
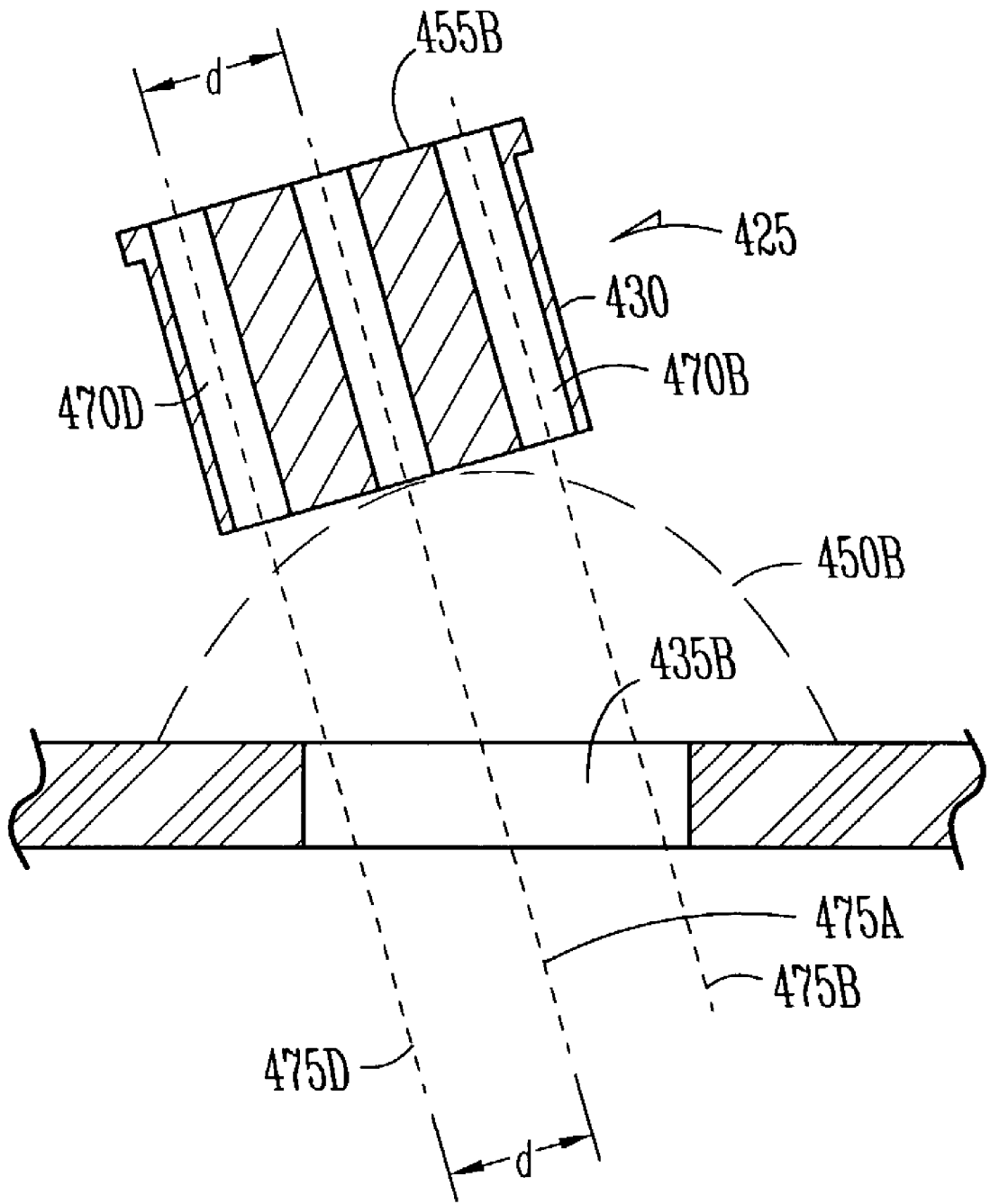
FIG. 4C is a conceptualized schematic diagram illustrating a cross-sectional side view of an instrument guide having one or more parallel lumens extending orthogonally through the instrument guide and having a limited range of motion.
Figure 4D:
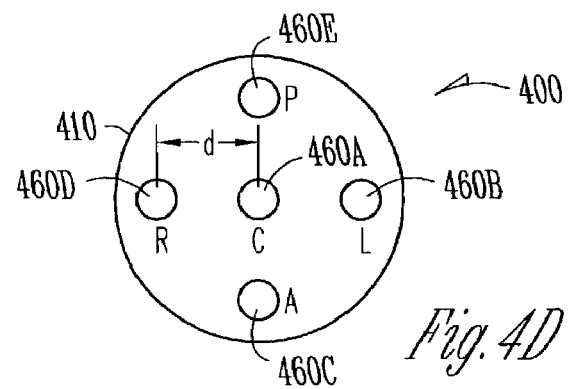
FIG. 4D is a conceptualized schematic diagram illustrating a top view of an instrument guide having at least one angled through-lumen extending through the instrument guide.
Figure 4E:
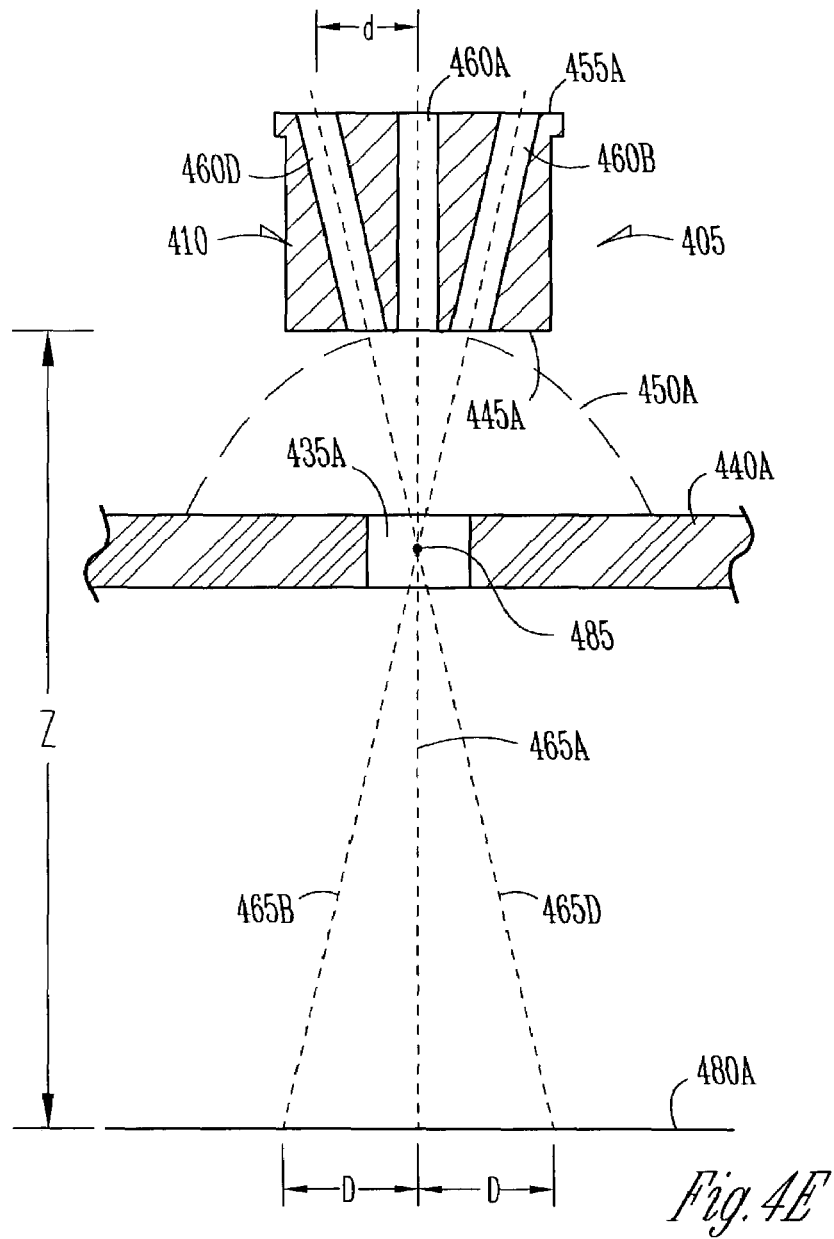
FIG. 4E is a conceptualized schematic diagram illustrating a cross-sectional side view of an instrument guide having at least one angled through-lumen extending through the instrument guide.

FIGS. 4A, 4B, 4C, 4D, and 4E are conceptualized schematic diagrams illustrating a top view 400 (FIG. 4D) and side view 405 (FIG. 4E) of an instrument guide 410 having at least one angled through-lumen, in comparison to a top view 420 (FIG. 4A) and side view 425 (FIG. 4B) of an instrument guide 430 having one or more parallel lumens extending orthogonally through the instrument guide 430. In this conceptualized schematic diagram, the instrument guides 410 and 430 are illustrated, for conceptual clarity, without being coupled to a respective base that is attached to the subject. However, it is understood that, in operation, the instrument guides 410 and 430 may be coupled to a tower-like base 105 or any other skull-mounted or frame-mounted base discussed in this document or known in the art. FIGS. 4B, 4C, and 4E illustrate respective burr hole entry portals 435A-B, in a subject's skull 440A-B, above which instrument guides 410 and 430 are respectively mounted.

In one example, such as discussed above with respect to FIG. 1, instrument guides 410 and 430 are coupled to the base 105 having a rotational joint (such as provided by the platform ring surface 302) and an arcuate sliding joint (such as provided by the saddle 130). In this manner, respective bottom surfaces 445A-B of the instrument guides 410 and 430 define respective planes tangential to semispheres 450A-B swept by adjusting the rotational and arcuate orientations provided by the base 105. In this example, the instrument guides 410 and 430 include respective top surfaces 455A-B defining respective planes that are substantially parallel to those defined by respective bottom surfaces 445A-B, however, the invention is not so limited, as discussed below.

In this example, the instrument guide 410 includes at least one instrument-guiding lumen 460A-E extending through the instrument guide 410 at an angle with respect to an axis 465A that extends through the instrument guide 410 aimed at the center of the entry portal 435A. (In one example, axis 465A is also orthogonal to one or both of the planes defined by the top surface 455A and the bottom surface 445A of the instrument guide 410). By contrast, the instrument guide 430 includes instrument-guiding lumens 470A-E extending through instrument guide 430 parallel to an axis 475A that extends through instrument guide 430 aimed at the center of the entry portal 435B. (In one example, axis 475A is also orthogonal to one or both of the planes defined by the top surface 455B and the bottom surface 445B. orthogonal to the planes defined by its top surface 455B and its bottom surface 445B of the instrument guide 430.) In the example illustrated in FIGS. 4A-4E, lumens 460A-E define corresponding coaxial trajectory axes 465A-E, and lumens 470A-E define corresponding coaxial trajectory axes 475A-E. These axes are illustrated as extending through respective entry portals 435A-B and intersecting respective target range planes 480A-B that are located within the subject at a distance Z from the respective bottom surfaces 445A-B.

The instrument guide 430 includes the offset lumen 470D, which is separated from the center lumen 470A by a distance d along the top surface 455B. Because these lumens define parallel axes 475A and 470D, such axes intersect target plane 480B with the same radial separation d, as illustrated in FIG. 4B. Moreover, because the instrument guide 430 is positioned at a distance above a burr hole entry portal 435B of a limited diameter, the adjustable orientation of the instrument guide 430 using the arcuate tilting of the saddle 130 will only be able to reach a relatively limited range of points on the target plane 480B, as depicted in FIGS. 4B and 4C.

The instrument guide 410 includes the offset lumen 460D, which is separated from the center lumen 460A by a like distance d along the top surface 455A. However, the coaxial axes 465D and 465A defined by the respective lumens 460D and 460A are configured to intersect at a common focus point 485, which is typically located at or beyond entry portal 435A (e.g., within the subject), but which can alternatively be located outside the subject above the entry portal 435A. This results in the axes 465D and 465A intersecting target plane 480A at points separated by a distance D. The angle between the axes 465D and 465A can be selected such that (for a given distance Z between the bottom surface 445A of the instrument guide 410) the axes 465D and 465A intersect the target plane 480A at the separation distance D, where the separation distance D at the target plane 480A is capable of exceeding the separation distance d at top surface 445A of the instrument guide 410. Moreover, the distance D is not limited to the radius of the burr hole entry portal 435A, but may instead exceed the radius of the burr hole entry portal 435A. Furthermore, using the arcuate tilting of the saddle 130, an even greater range of points on the target range plane 480A will be accessible by using the instrument guide 410. In addition, the instrument guide 410 will be able to accommodate more arcuate tilting than the instrument guide 430 because the angled trajectory axes are more focused within the entry portal 435A than the parallel trajectory axes are within the similarly-sized entry portal 435B. This will further extend the accessible area on target plane 480A beyond that accessible on target plane 480B. Additionally or alternatively, the focused trajectory axes allow use of a smaller burr hole 435A, as illustrated in FIG. 4E.

In the illustrative example of FIG. 4D, the instrument guide 410 includes a center lumen 460A (labeled "C" in FIG. 4D), defining a corresponding coaxial trajectory axis 465A aimed at the center of entry portal 435A. In this example, a "right" offset lumen 460D (labeled "R" in FIG. 4D), defining a corresponding coaxial trajectory axis 465D, is separated from the center lumen 460A at the top surface 455A by a center-to-center distance d. In this example, a "left" offset lumen 460B (labeled "L" in FIG. 4D), defining a corresponding coaxial trajectory axis 465B, is separated from the center lumen 460A at the top surface 455A by a like center-to-center distance d. In this example, a "posterior" offset lumen 460E (labeled "P" in FIG. 4D), defining a corresponding coaxial trajectory axis 465E (not shown), is separated from the center lumen 460A at the top surface 455A by a like center-to-center distance d. In this example, an "anterior" offset lumen 460C (labeled "A" in FIG. 4D), defining a corresponding coaxial trajectory axis 465C (not shown), is separated from the center lumen 460A at the top surface 455A by a like center-to-center distance d. Axes 465A-E intersect at a focus point 485. In the illustrative example of FIG. 4E, the focus point 485 is located at the entry portal 435A. However, the focus point 485 can alternatively be located at or beyond entry portal 435A (i.e., within the subject), or even located outside the subject above the entry portal 435A. For example, the focus point 485 may be located beyond the entry portal 435A, i.e., deeper within the subject, either by: (1) altering the angle between the offset lumens 460B-E and the orthogonal center axis 460A; or (2) altering the height of the instrument guide 410 above the entry portal 435, or both (1) and (2).

In one example, trajectory guide assembly 100 is prepared as a kit providing multiple different instrument guides 110. Each instrument guide 110 in the kit provides a predetermined distance d and a predetermined offset lumen angle 140 that obtains a different resulting predetermined distance D at a given height of the instrument guide 110 above the entry portal 115. In a further example, the height of the instrument guide 110 above the entry portal 115 is also adjustable. This, in turn, adjusts the depth of the focus point 485. For example, in operation in a brain surgery application, positioning the focus point 485 at a single cortical entry point just beneath the entry portal 435A reduces trauma to the subject's brain.

In one example, the height of the instrument guide 110 above the entry portal 115 is adjusted by inserting a washer-like spacer (having a predetermined thickness) over the barrel sleeve 306 of the instrument guide 110 before the barrel sleeve 306 is inserted into the opening 310 in the ball 304. In this example, the trajectory guide assembly 100 is prepared as a kit with multiple spacers of different predetermined thicknesses to adjust the height of the instrument guide 110 above the entry portal 115. The user can select the appropriate spacer that adjusts the height of the instrument guide 110 above the entry portal 115 to obtain, for example: the desired depth of focus point 485; the desired depth of the target plane 480A corresponding to the predetermined distance D; or, to adjust the value of D for a target plane 480A at a given depth beneath the entry portal 435A. In one example, the trajectory guide kit includes printed instructions or a computer program providing the necessary computations to assist the user in selecting the appropriate height of the instrument guide 110 for obtaining the desired access to accomplish one or more of these various objectives. In a further example, at least some of such information is printed on the spacers.

Figure 5C:
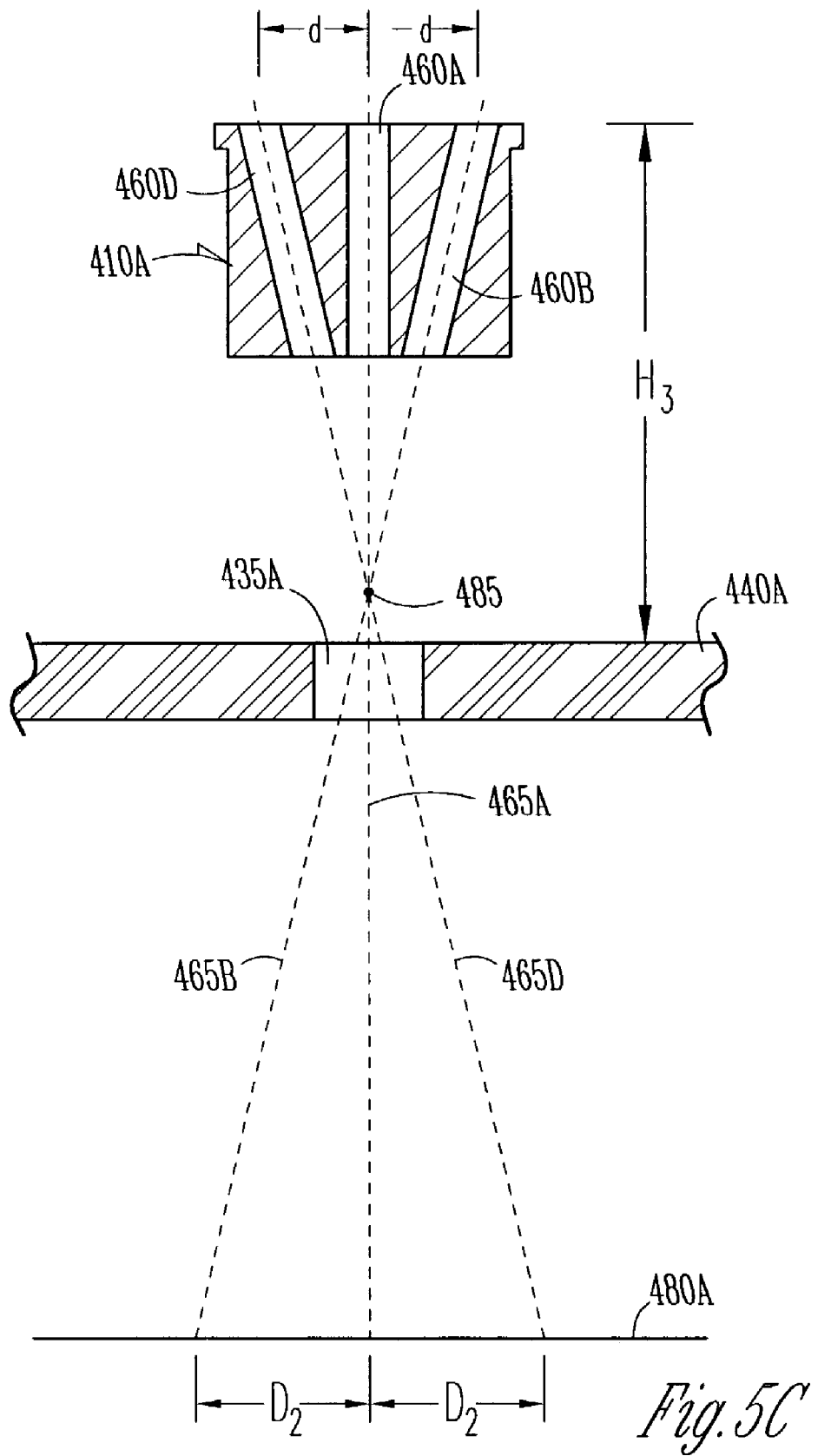

FIGS. 5A-5F are cross-sectional schematic diagrams illustrating conceptually various operative embodiments of an instrument guide having at least one angled through-lumen. In FIG. 5A, the instrument guide 410A is positioned such that its top surface is at a height H1 above the entry portal 435A in the skull 440A. The target plane 480A is located at a distance Z1 below the bottom surface of the instrument guide 410. In this example, the lumens 460 are configured to intersect at a single cortical entry point 485 at the surface of the subject's brain just beneath the entry portal 434A. Using this single cortical entry point 485 reduces trauma to the subject's brain. The axes 465A and 465D are separated by a distance d at the top surface of the instrument guide 410, as are the axes 460A and 460B. The axes 465A and 465D intersect the target plane 480A at points that are separated by a distance D1, as do the axes 460A and 460B.

In FIG. 5B, the instrument guide 410A is positioned closer to the entry portal 435A (i.e., H2<H1) and/or the angles between the axes 465A and 465D and between the axes 465A and 465B are decreased (as compared to FIG. 5A). Consequently, the axes 465A, 465B, and 465D intersect at a single focus point 485 located beyond entry portal 435A within the subject. This deeper focus point 485 may be useful, for example, to avoid a nearby critical area 500 that may be located at least partially beneath the entry portal 435A.

In FIG. 5C, the instrument guide 410A is positioned farther from the entry portal 435A (i.e., H3>H1) and/or the angles between the axes 465A and 465B are increased (as compared to FIG. 5A). Consequently, the axes 465A, 465B, and 465D intersect at a single focus point 485 located above the entry portal 435A and outside the subject. In this example, because the axes are still more focused within the entry portal 435A than the parallel axes of the instrument guide 430 of FIG. 4B, the embodiment of FIG. 5C still obtains wider accessibility of points on the target plane 480A than would the parallel axes of the instrument guide 430 of FIG. 4B.

Figure 5E:
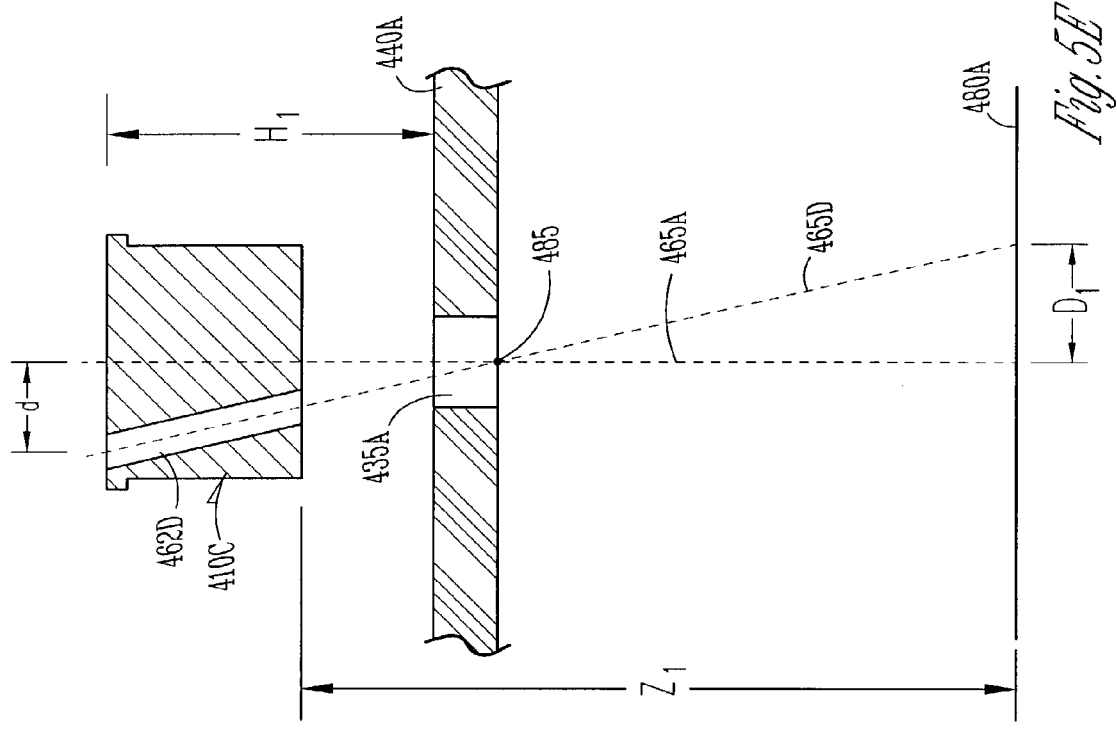
Figure 5D:
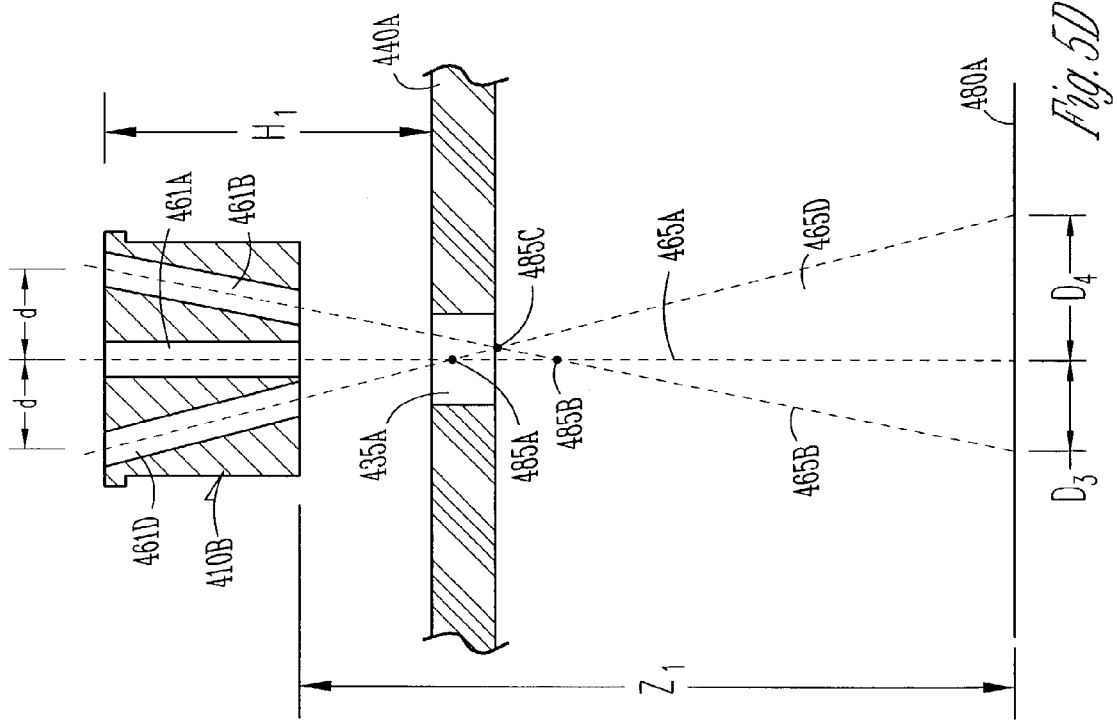

FIG. 5D illustrates an example in which lumens 461A, 461B, and 461D through instrument guide 410B define corresponding coaxial axes 465A, 465B, and 465D need not, and do not, intersect at a single focus point. Instead, the axes 465A and 465B intersect at a point 485B, and the axes 465A and 465D intersect at a different point 485A, and the axes 465B and 465D intersect at yet another point 485C.

FIG. 5E illustrates an example in which the center lumen 460A is omitted from instrument guide 410C. In this example, the instrument guide 410C includes at least one lumen, such as the lumen 462D defining a coaxial axis 465D that intersects, at a focus point 485, an orthogonal axis 465A through top and bottom surfaces of the instrument guide 410C. This example may be useful, for example, in obtaining access to points beyond the radius of the burr hole entry portal 435A.

Figure 5F:
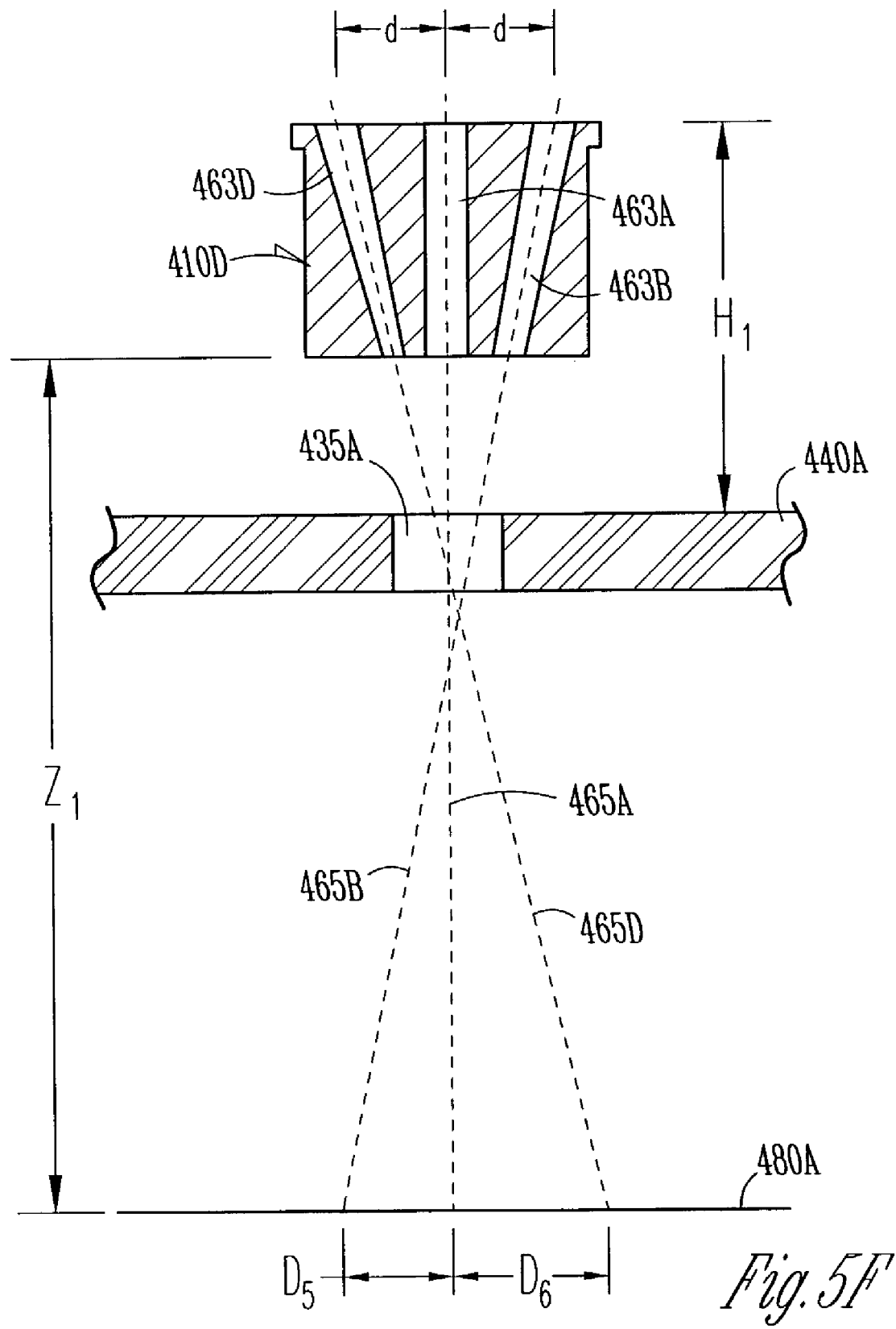

FIG. 5F illustrates an example in which none the axes 465A, 465B, and 465D through instrument guide 410D intersects another one of the axes 465A, 465B, and 465D. This example may be useful, for example, in inserting needles or other instruments concurrently into each of the lumens 463A, 463B, and 463D respectively corresponding to the axes 465A, 465B, and 465D. Alternatively, at least one of the axes 465A, 465B, and 465D does not intersect another one of the axes 465A, 465B, and 465D. FIGS. 5A-5F are merely illustrative examples; other variations are also possible.

Figure 6:
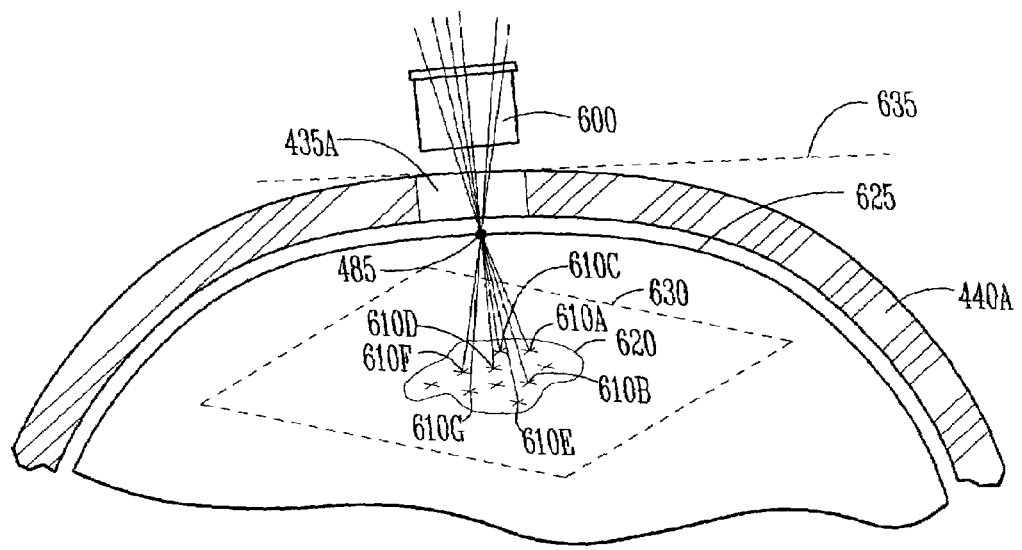
FIG. 6 is a conceptualized side view of an instrument guide including lumens arranged in a predetermined pattern.
Figure 7:
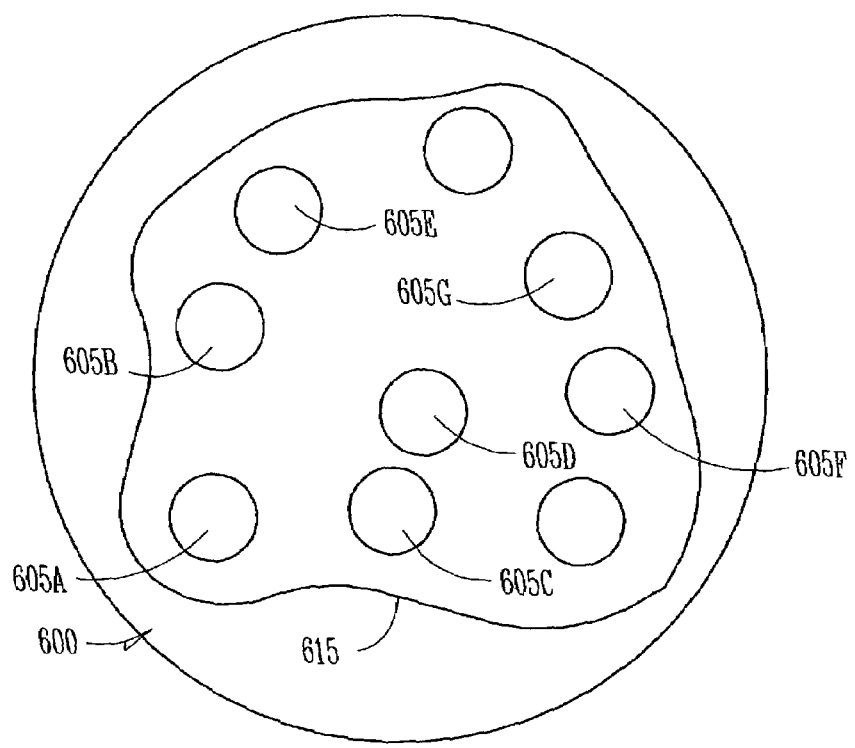
FIG. 7 is a conceptualized top view (along the cutline 7-7 of FIG. 6) of an instrument guide including lumens arranged in a predetermined pattern.

FIGS. 6 and 7 are a conceptualized side view (FIG. 6) and a top view (FIG. 7), respectively, of an instrument guide 600 including lumens 605A-G arranged in a predetermined pattern 615 that is a mirror image of a desired pattern 620 in a target range plane 630, which is parallel to an entry plane 635 defined by the entry portal 435A. Lumens 605A-G define respective coaxial axes that converge upon and intersect at focus point 485, which, in this example, is located on the surface of the subject's cortex 625 adjacent to and just beyond the entry portal 435A. The coaxial axes defined by the lumens 605A-G intersect the target plane 630 in the desired pattern 620 for which the mirror image pattern 615 was designed to obtain.

In one example, the desired pattern 620 represents an anatomical, pathological, or other clinically relevant feature within the brain. In one illustrative example, the desired pattern 620 may be shaped similarly to a tumor or lesion, having a particular shape, for which treatment by a primary instrument (guided by instrument guide 600) is desired. In another illustrative example, the desired pattern 620 is shaped like the subject's putamen and/or caudate nucleus—anatomical regions of the subject's brain that may benefit from, among other things, transplanted fetal nigral cells for treating Parkinson's disease. Similarly, mirror image guide lumen pattern 615 may be configured to obtain any other desired pattern shape 620 and/or target distribution at a particular depth, whether to match an anatomical or pathological feature or to obtain any other clinically desirable instrument access. Moreover, by adjusting a height of instrument guide 600 above entry portal 435A, the same pattern shape 620 can be obtained in three dimensions for various target range planes 630 located at different depths beneath entry portal 435A. Alternatively or additionally, trajectory guide assembly 100 is configured as a kit with multiple instrument guides 600 for obtaining the same or different patterns 620 at the same or different depths beneath entry portal 435A.

Although FIGS. 6 and 7 were discussed above with respect to an instrument guide 600 having a predefined pattern of holes that collectively obtain a desired pattern on a target range plane 630, in an alternate example, a "multipurpose" or "universal" instrument guide 600 is used. Such a multipurpose instrument guide 600 select between more than one target pattern on the target range plane 630. In one example, the particular resulting target pattern results from which particular ones of lumens 605 are selected for inserting an instrument therethrough. In one such example, a printed user manual (or computer software) is used to instruct the user which particular lumens to select and utilize for inserting the instrument (and/or which particular lumens to avoid using) thereby obtaining the desired pattern. In one example, the user marks those lumens through which the instrument will be inserted by pressing a colored (or otherwise identifiable) guide bushing into such selected lumens (or alternatively, by inserting a plug into those lumens that are to be avoided for obtaining the desired pattern). In one example, the tops of such lumens are countersunk to receive such guide bushings.

Other Exemplary Bases

FIGS. 1-3 illustrate an example of the instrument guide 110 used in conjunction with one example of the base 105, however, the instrument guide 110 may be used with a wide variety of skull-mounted or frame-mounted bases. FIGS. 4-7 illustrate operative examples of instrument guides 410 and 600 that are independent of the particular base used for the instrument guide.

Figure 8:
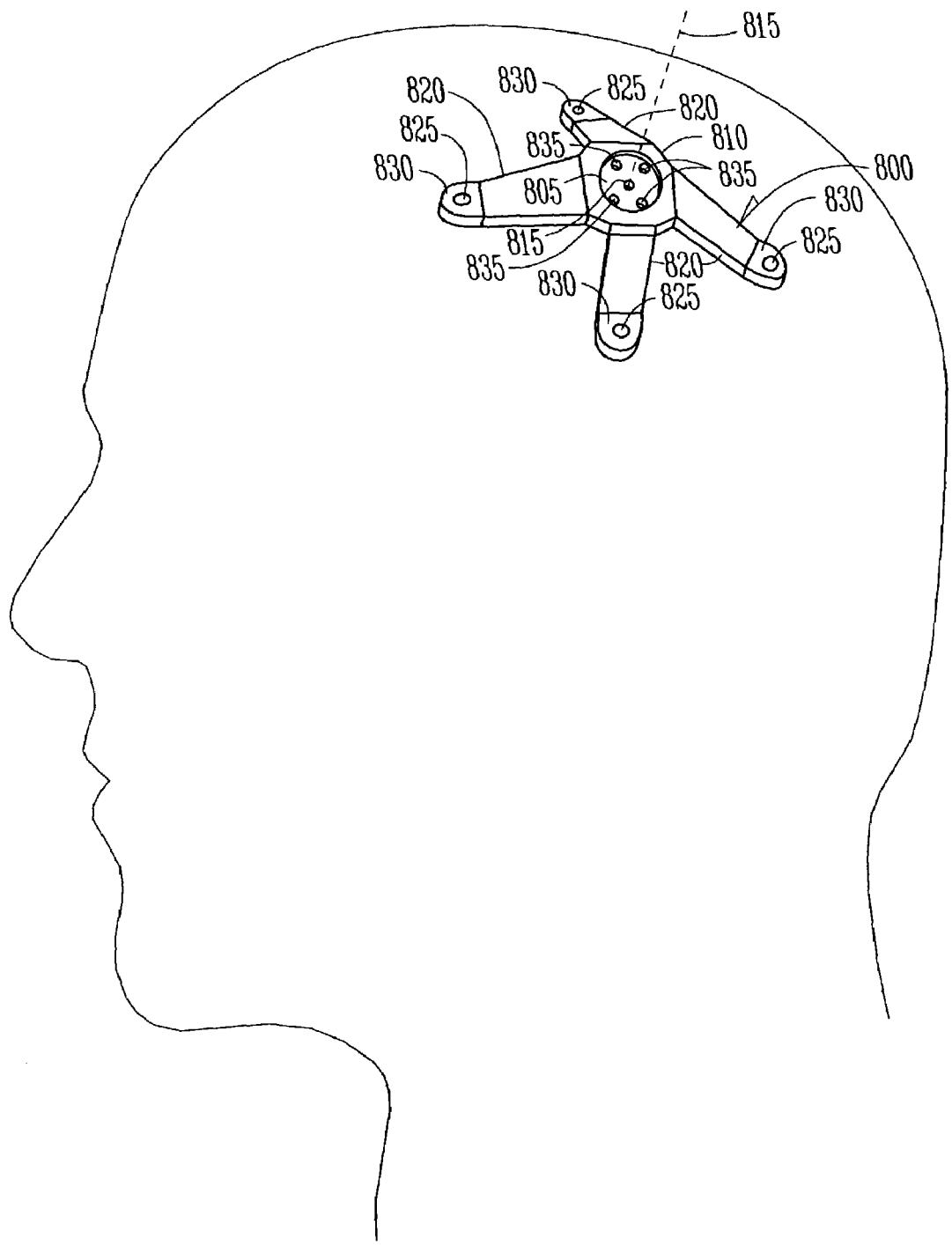
FIG. 8 is an example of a trajectory guide base that is custom-formed such that an instrument guide portion of a working platform includes an axis extending orthogonally therethrough and directed through a burr hole or other entry portal to intersect the desired target within the subject.

FIG. 8 is an example of a trajectory guide base 800 that is custom-formed (e.g., using known rapid prototyping and tooling techniques and preoperative images of a desired target in a subject) such that an instrument guide 805 portion of a working platform 810 includes a center axis 815 (e.g., extending orthogonally therethrough) wherein center axis 815 is directed through the center of a burr hole or other entry portal such that center axis 815 intersects a portion of the desired target within the subject. In one example, platform 810 is oriented as desired by customizing the size or shape of legs 820, which are mounted to the subject's skull, such as by using bone screws extending through holes 825 through respective feet 825 extending outwardly from respective legs 820. In this example, instrument guide 805 includes at least one instrument-guiding lumen 835, which defines a coaxial axis therethrough that is angled with respect to center axis 815 (e.g., as discussed above). In one example, multiple different instrument guides 805 are capable of being snap-fitted or otherwise inserted into platform 810, providing lumens defining different coaxial patterns and/or providing various heights of the top surface of the instrument guides 805 above the entry portal. In a further example, such insertion of one or more instrument guides 805 into platform 810 uses one or more spacers, an adjustable coupling, or any other height adjustment device. Base 800, or any of the other bases discussed in this document, may be mounted to skull-mounted fixtures for carrying fiducial markers recognizable on an imaging system, such as a frameless surgical navigation system, a magnetic resonance imaging system, etc.

Figure 9:
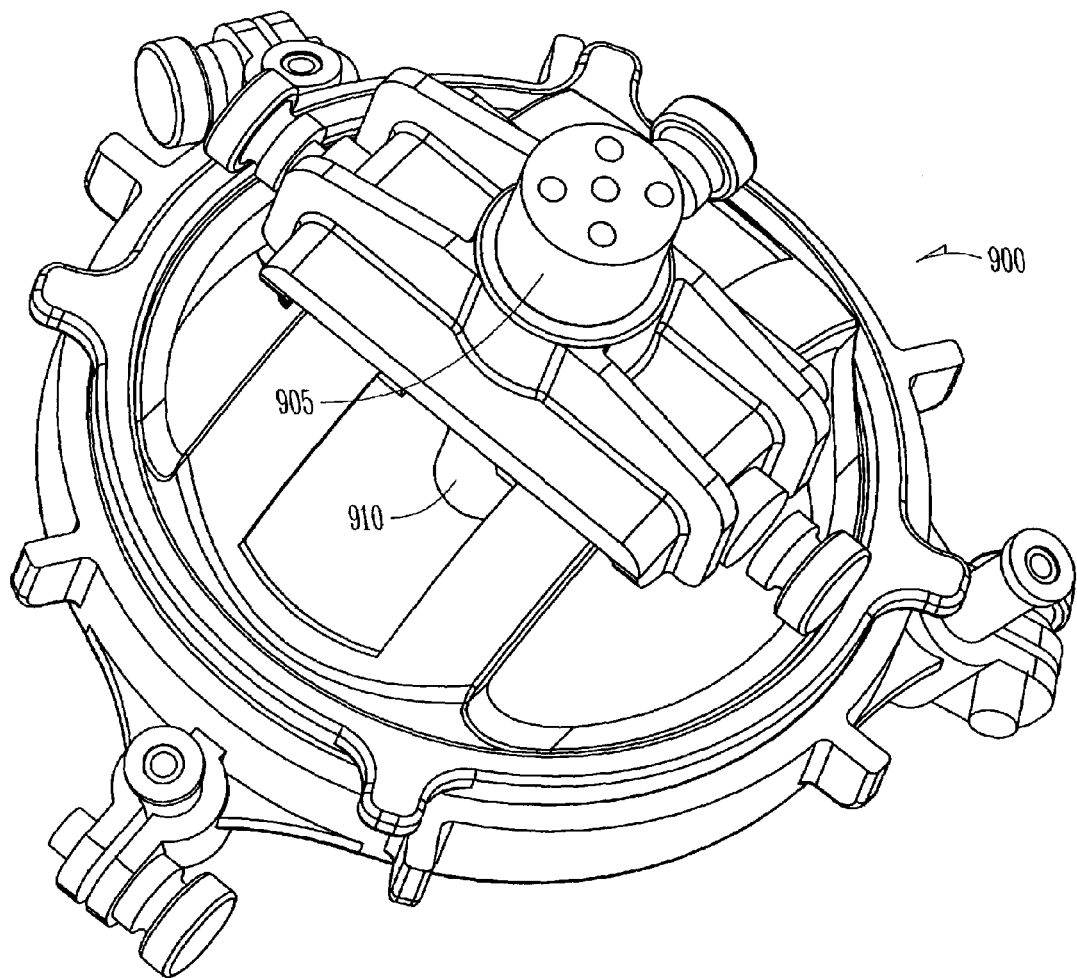
FIG. 9 is a schematic diagram illustrating generally, by way of example, but not by way of limitation, one embodiment of a first alternative trajectory guide base carrying an instrument guide having angled lumen(s).

FIG. 9 is a schematic diagram illustrating generally, by way of example, but not by way of limitation, one embodiment of an alternative trajectory guide base 900 carrying an instrument guide 905 having at least one lumen that is angled with respect to a center axis aimed at the center of the underlying entry portal. In one example, instrument guide 905 configured substantially as described above with respect to instrument guide 410, and having a barrel sleeve portion 910 such as described above with respect to instrument guide 110. Certain portions of trajectory guide base 900 are described in Matthew Solar's U.S. patent application Ser. No. 10/325,615, entitled ORGAN ACCESS DEVICE AND METHOD, filed on Dec. 20, 2002, assigned to Image-Guided Neurologics, Inc., which is incorporated herein by reference in its entirety, including its description of a trajectory guide base as illustrated in FIG. 9 of the present document.

Figure 10:
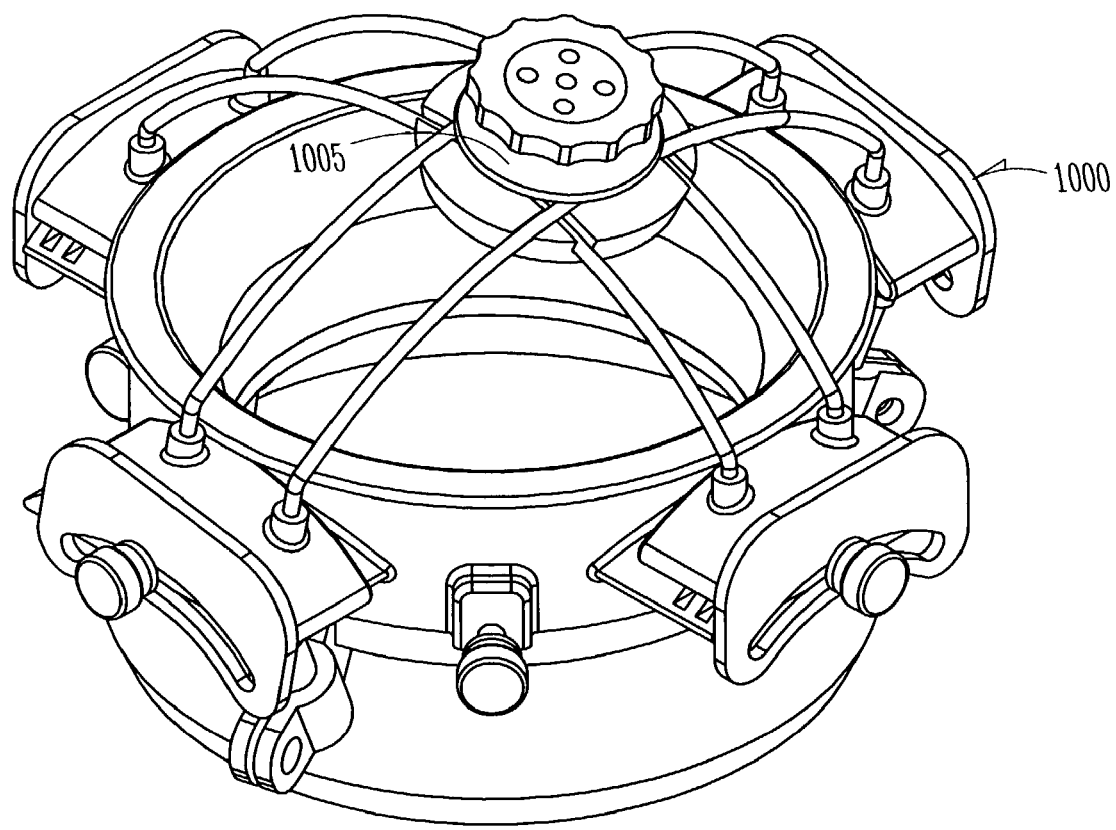
FIG. 10 is a schematic diagram illustrating generally, by way of example, but not by way of limitation, another embodiment of a second alternative trajectory guide base carrying an instrument guide having angled lumen(s).

FIG. 10 is a schematic diagram illustrating generally, by way of example, but not by way of limitation, another embodiment of an alternative trajectory guide base 1000 carrying an instrument guide 1005 having at least one lumen that is angled with respect to a center axis aimed at the center of the underlying entry portal, e.g., such as described above with respect to instrument guide 410. Certain portions of trajectory guide base 1000 are described in Matthew Solar's U.S. patent application Ser. No. 10/325,615, entitled ORGAN ACCESS DEVICE AND METHOD, filed on Dec. 20, 2002, assigned to Image-Guided Neurologics, Inc., which is incorporated herein by reference in its entirety, including its description relevant to a trajectory guide base as illustrated in FIG. 10 of the present document.

Figure 11:
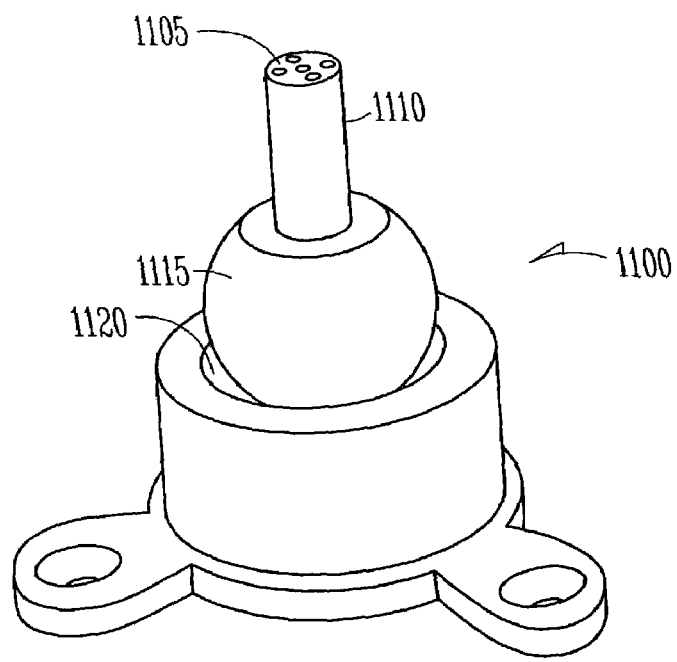
FIG. 11 is a schematic diagram illustrating generally, by way of example, but not by way of limitation, another embodiment of a third alternative trajectory guide base carrying an instrument guide having angled lumen(s).

FIG. 11 is a schematic diagram illustrating generally, by way of example, but not by way of limitation, another embodiment of an alternative trajectory guide base 1100 carrying an instrument guide 1105 having at least one lumen that is angled with respect to a center axis aimed at the center of the underlying entry portal, e.g., as described above with respect to instrument guide 410, and having a barrel sleeve portion 1110 such as described above with respect to instrument guide 110. In this example, barrel sleeve 1110 extends into a ball 1115 that is received within a socket 1120 portion of base 1100. In this example, ball 1115 is positioned just above a burr hole entry portal. Certain portions of trajectory guide base 1100 are described Truwit U.S. Pat. No. 6,267,769, which is incorporated herein by reference in its entirety, including its description relevant to a trajectory guide base as illustrated in FIG. 11 of the present document.

Figure 12:
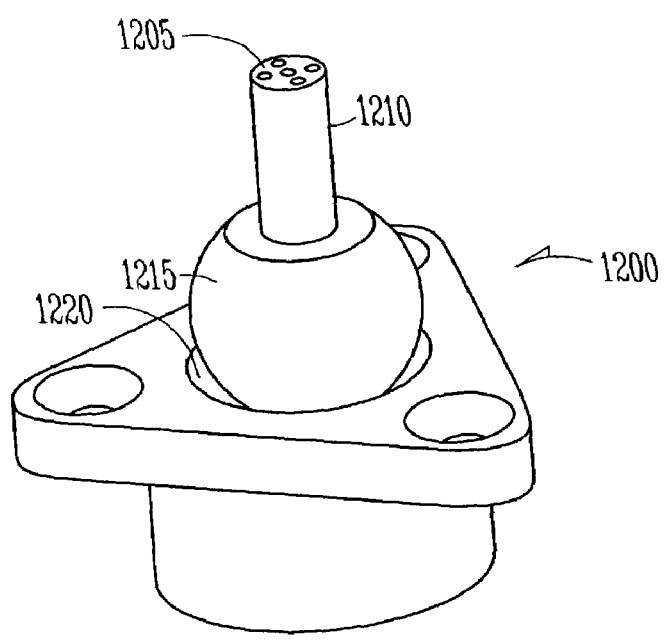
FIG. 12 is a schematic diagram illustrating generally, by way of example, but not by way of limitation, another embodiment of a fourth alternative trajectory guide base carrying an instrument guide having angled lumen(s).

FIG. 12 is a schematic diagram illustrating generally, by way of example, but not by way of limitation, another embodiment of an alternative trajectory guide base 1200 carrying an instrument guide 1205 having at least one lumen that is angled with respect to a center axis aimed at the center of the underlying entry portal, e.g., as described above with respect to instrument guide 410, and having a barrel sleeve portion 1210 such as described above with respect to instrument guide 110. In this example, barrel sleeve 1210 extends into a ball 1215 that is received within a socket 1220 portion of base 1200. In this example, ball 1215 is positioned at least partially within a burr hole entry portal. Certain portions of trajectory guide base 1200 are described Truwit U.S. Pat. No. 5,993,463, which is incorporated herein by reference in its entirety, including its description relevant to a trajectory guide base as illustrated in FIG. 12 of the present document.

Figure 13:
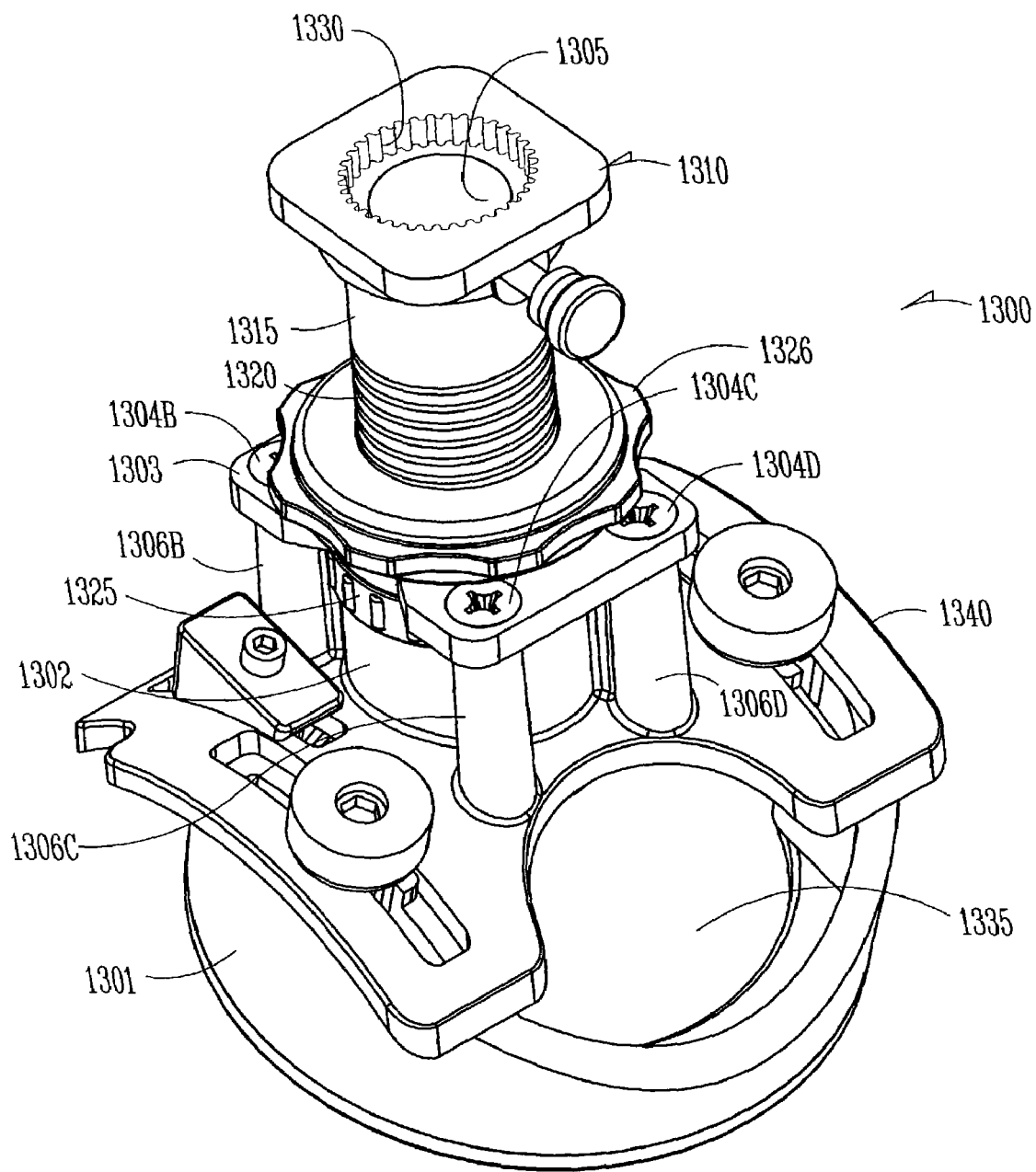
FIGS. 13 and 14 are respective top and bottom perspective views illustrating generally, by way of example, but not by way of limitation, an alternative trajectory guide base providing, among other things, a stage having an adjustable height above the entry portal.
Figure 14:
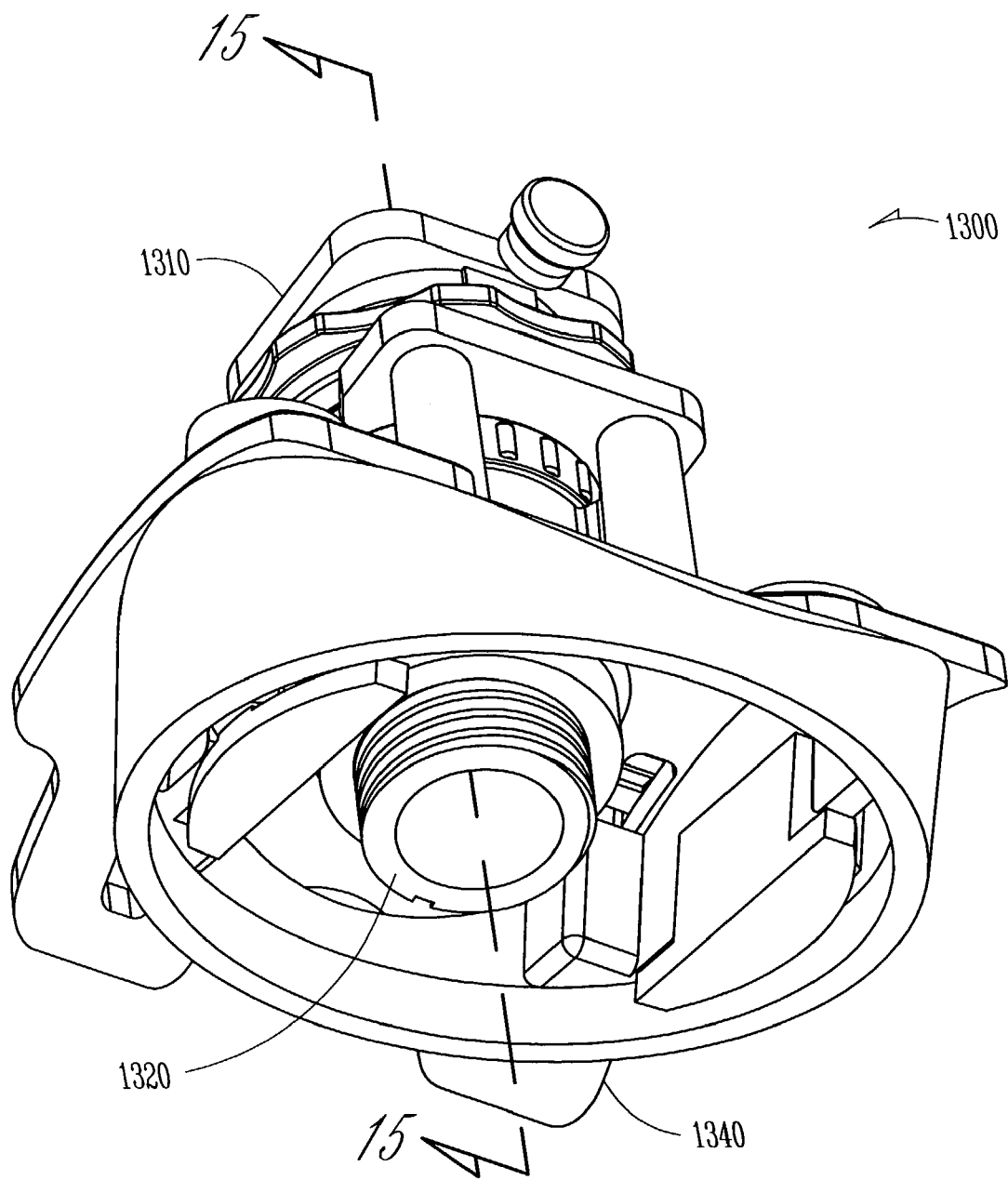

FIGS. 13 and 14 are respective top and bottom perspective views illustrating generally, by way of example, but not by way of limitation, an alternative trajectory guide base 1300, similar in certain respects to the base 105 of FIG. 1 (e.g., capable of rotatably riding on a platform ring and including an arcuate saddle movement for tilting a trajectory angle with respect to a normal axis from center of the entry portal). In the examples of FIGS. 13 and 14, the base 1300 includes a rotatable cylinder 1301 having an arced upper end upon which a tilting saddle 1340 rides. The saddle 1340 includes an upwardly extending cylinder 1302. A rotatable dial 1325 rests upon a top end of the cylinder 1302. The dial 1325 is captured against the top end of the cylinder 1302 by an overlying plate-like retainer collar 1303. The collar 1303 is secured to the saddle 1340 by screws 1304A-D, which are received into corresponding screw mounts 1306A-D, which rise upward from the saddle 1340.

In this example, the trajectory guide base 1300 includes a receptacle 1305 that is sized and shaped to receive a barrel sleeve (or other portion) of an instrument guide. In one example, the received instrument guide includes at least one lumen that is angled with respect to a center axis aimed at the center of the underlying entry portal, e.g., as described above with respect to the instrument guide 410. In the example illustrated in FIGS. 13 and 14, the base 1300 includes a stage 1310. The stage 1310 includes an outwardly protruding sleeve 1315 through which the receptacle 1305 extends. In this example, the sleeve 1315 includes external threads 1320 that engage corresponding internal threads on a captured rotatable receiving collar dial 1325. In this example, the dial 1325 includes ridges, texture, or other features that make it easier to grip and rotate the dial 1325. By rotating the dial 1325, the stage 1310 rides up or down on the internal threads of the dial 1325. In this manner, the dial 1325 and the threads 1320 of the sleeve 1315 provide an adjustable coupling device for adjusting a height of the stage 1310 above the entry portal. This, in turn, adjusts the height of the top surface of any instrument guide that is inserted into the stage 1310. When the desired height is obtained, that height is secured by turning a nut 1326, which, in turn, wedges an underlying bushing against sleeve 1315.

In one example, an interior portion of the receptacle 1305 includes circumferential gear teeth 1330 that mate with and engage corresponding circumferential gear teeth on a cylindrical outer portion of the instrument guide inserted therein. This prevents the instrument guide from rotatably slipping within the receptacle 1305 unless the instrument guide is intentionally lifted out, rotated, and re-inserted into the receptacle 1305. This example also includes a cutout portion of the saddle 1340 riding on an arcuate joint of base 1300. This allows viewing and access of the instrument being inserted through the instrument guide received in receptacle 1305, as discussed above. Such viewing and access enhances both safety and usability of any surgical or other procedures being performed using the instrument.

Figure 15:
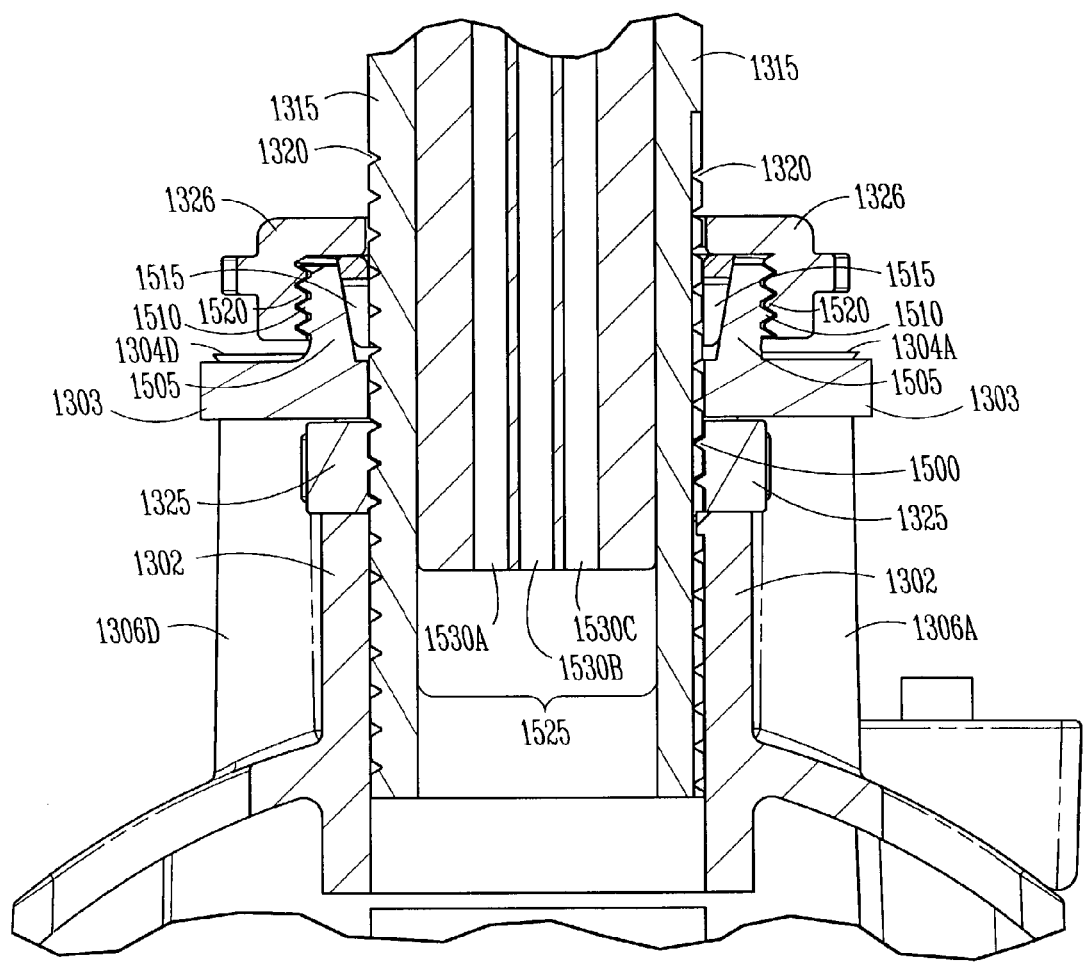
FIG. 15 is a cross-sectional view, taken along the cutline 15-15 of FIG. 14.

FIG. 15 is a cross-sectional view, taken along the cutline 15-15 of FIG. 14. Among other things, FIG. 15 illustrates further details relevant to the adjustable height coupling for varying the height of the stage 1310 above the entry portal. FIG. 15 further illustrates one example of how the dial 1325 is captured between the underlying cylinder 1302 and the overlying collar 1303. In this example, the collar 1303 is secured to the saddle 1340 via screws 1304A-D that are inserted into corresponding screw mounts 1306A-D. The internal cylindrical circumference of the dial 1325 includes one or more threads 1500 that engages one or more of the threads 1320 on the external cylindrical circumference of the sleeve 1315 upon which the stage 1310 rests. Using such a threaded adjustable height coupling, the sleeve 1315 (and the attached stage 1310) is moved up and down by rotating the dial 1325.

In the example of FIG. 15, the collar 1303 includes an upwardly rising cylinder 1505. An external circumference of the cylinder 1505 includes one or more threads 1510. An internal circumference of the cylinder 1505 is tapered, such as to receive an approximately circular or cylindrical wedge bushing 1515 therein. The nut 1326 includes internal circumferential threads 1520 that engage the external circumferential threads 1510 of the cylinder 1505. After the height of the stage 1310 is threadably adjusted, such as discussed above, the resulting height is secured by rotating the nut 1325, which forces the wedge bushing 1515 downward and inward against the sleeve 1315.

The example of FIG. 15 also illustrates an instrument guide 1525 inserted within the sleeve 1315. In one example, instrument guide 1525 includes at least one instrument-guiding through lumen that is angled with respect to an axis aimed at the center of the underlying burr hole entry portal. However, it should be understood that the height adjustment mechanism illustrated in FIG. 15 can also be used with an instrument guide 1525 having lumens 1530A-C that are at or parallel to an axis aimed at the center of the underlying burr hole entry portal, such as illustrated in FIG. 15.

Range-Compensated Instrument Guide Example

FIG. 16A is a cross-sectional schematic diagram, similar in certain respects to that of FIG. 5A, but illustrating generally one example of an instrument guide 1600 having a top surface 1605 that is curved, faceted, or otherwise designed to obtain, for each axis 465A-D extending coaxially through a corresponding trajectory guide lumen 460A-D, a fixed length L between the top surface 1605 and a range plane 480A that is parallel to the entry plane that is tangential to the burr hole or other entry portal 435A. This allows a biopsy needle 1610 (or other instrument) having a length L (for example, fixed by setting a depth stop 1615), as illustrated in FIG. 16B, to be inserted through any of the lumens 460A-D (e.g., using a handle 1617). The distal tip 1620 will reach the target plane 480A-regardless of the particular lumen 460A-D through which the needle 1610 is inserted), despite the fact that some of these axes 465B-D are angled with respect to an axis 465A that is aimed at the center of the entry portal 435A.

Example of Manufacturing Instrument Guide

Figure 17:
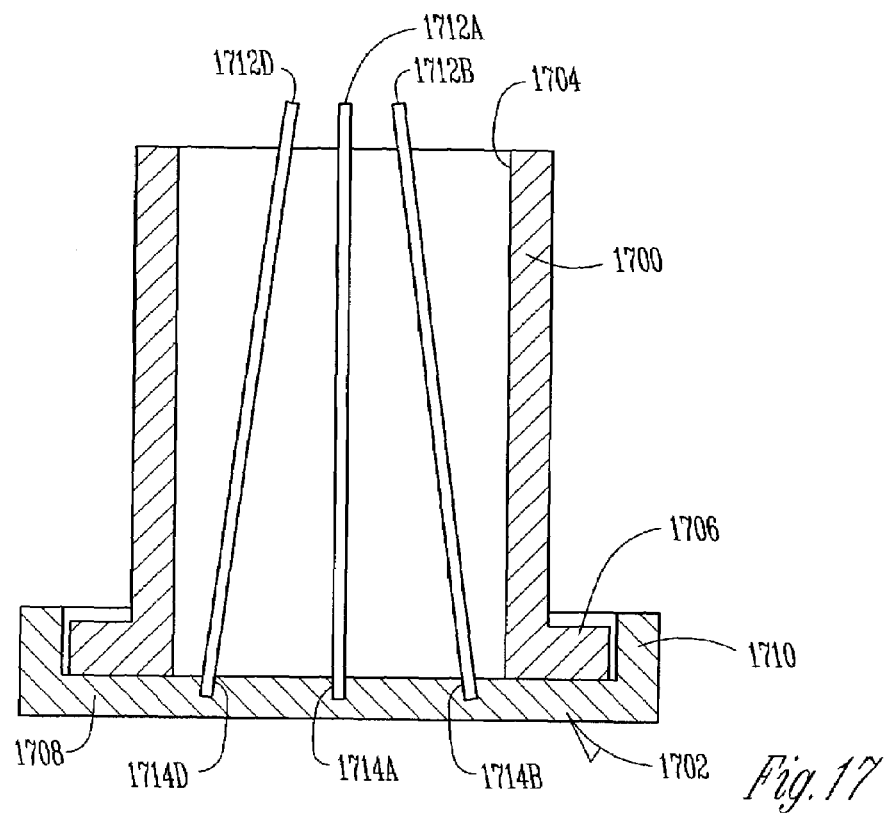
FIG. 17 is a cross-sectional schematic drawings illustrating generally aspects of one technique for manufacturing an instrument guide.
Figure 18:
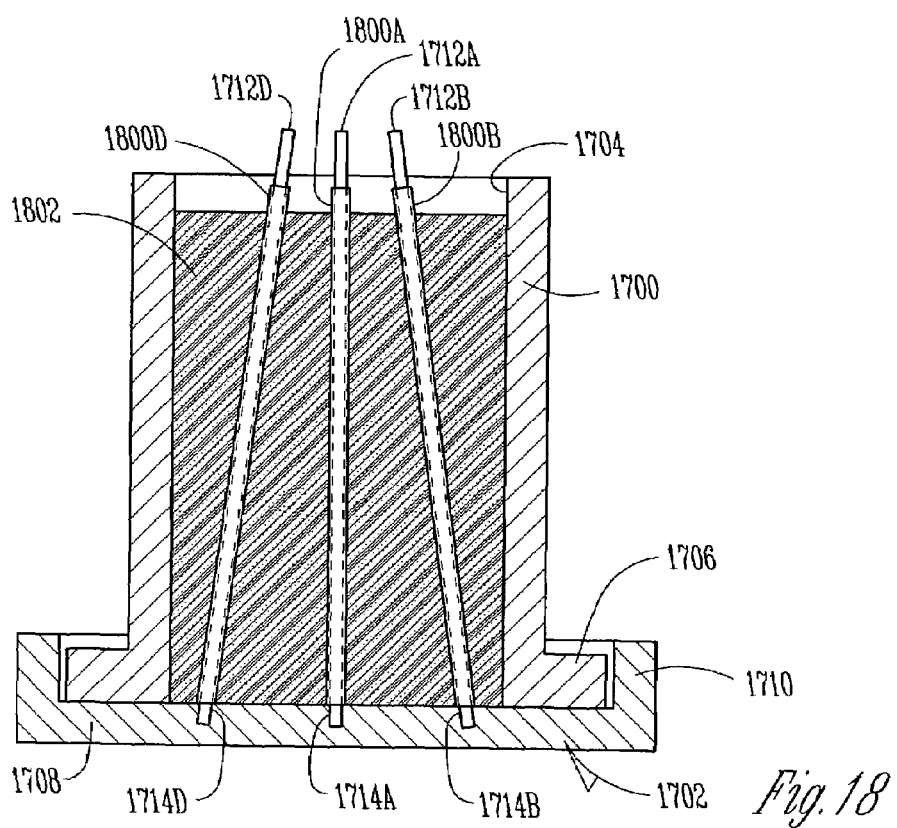
FIG. 18 is a cross-sectional schematic drawings illustrating generally further aspects of a technique for manufacturing an instrument guide.

FIGS. 17 and 18 are cross-sectional schematic drawings illustrating generally, by way of example, but not by way of limitation, one technique for manufacturing an instrument guide having at least one angled lumen (such as the instrument guide 410, for example). However, the devices and techniques illustrated in FIGS. 17 and 18 are also useful for manufacturing an instrument guide having parallel lumens (such as the instrument guide 420, for example).

In the example illustrated in FIG. 17, a molding plug/bushing 1700 is first inserted into a fixture 1702. In this example, the bushing 1700 is a plastic or other hollow cylinder including a lumen 1704 and a ring-like circumferential lip 1706. In this example, the bushing 1700 defines the outer circumferential shape of the completed instrument guide 410. The fixture 1702 includes a circular base 1708 and a circumferential seating ring 1710 rising orthogonally outward therefrom. The ring 1710 is sized and shaped to snugly receive the bushing 1700 therewithin. The fixture 1702 includes insertable and removable rods or pins 1712A-E. Such pins 1712A-E will define the corresponding lumens 460A-E of the completed instrument guide 410, as discussed below. In the illustrated example, the removable pins 1712A-E are inserted snugly within respective appropriately oriented receptacles 1714A-E in the circular base 1708, with such insertion occurring either before or after the bushing 1700 is seated within the ring 1710 of the fixture 1702.

In FIG. 18, tubes 1800A-E are then slipped over the respective pins 1712A-E. The lumens of these tubes 1800A-E will provide the corresponding lumens 460A-E of the completed instrument guide 410. In one example, the tubes 1800 are thin metal tubes having a wall thickness of about 0.003 inches.

After the hollow tubes 1800A-E have been slipped over the respective pins 1712A-E, the interstices between the tubes 1800A-E, e.g., within the lumen 1704 of the bushing 1700, are filled with liquid epoxy (or any other flowable hardening agent). This epoxy solidifies to form a solid plug 1802. The solid plug 1802 holds and carries the tubes 1800A-E in the orientation defined by their respective pins 1712A-E. The pins 1712A-E are then removed from the base 1708 of the fixture 1702. The lumens of the tubes 1800A-F then provide the respective lumens 460A-E of the completed instrument guide 410. The completed instrument guide 410 (which includes the bushing 1700, the tubes 1800A-E, and the solid plug) is then removed from the fixture 1702.

The above described method of manufacture is well-suited for manufacturing an instrument guide 410 having one or more angled lumens, which would generally be incompatible with a plastic molding process. Moreover, drilling such lumens is limited by the accuracy of drilling, which may be subject to wander of the drill bit. The above described method of manufacture is also well-suited for manufacturing an instrument guide 420 having parallel lumens. Although parallel lumens are not wholly incompatible with a plastic molding process, such a plastic molding process would likely result in tapered lumens. By contrast, the tubes 1800A-E are capable of providing lumens of uniform circumference. Moreover, the above described method is applicable to manufacturing an instrument guide having any number of one or more lumens used for providing trajectory guidance or for any other purpose.

CONCLUSION

The various bases discussed in this document are presented as illustrative examples, and are not intended to be limiting. The instrument guides discussed in this document that have at least one lumen angled with respect to a center axis aimed at the center of the underlying entry portal will be capable of use with other skull-mounted or frame-mounted bases. Moreover, the techniques discussed herein are not limited to targeting locations within a subject's brain, but are also applicable to targeting other locations within a subject. Furthermore, the techniques discussed herein may also be useful for accessing locations within any material, particularly where access to the material is limited by a finite-sized entry portal.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:

1. An apparatus comprising:
a base, sized and shaped to be secured in or about a pre-existing entry portal in a human or animal subject that includes a target within the subject beyond the entry portal, the entry portal defining an entry plane, and the target defining a target plane that is substantially parallel to the entry plane; and
an instrument guide, coupled to the base and configured to be oriented with respect to the base to define a first axis extending through the instrument guide and the entry portal toward the target, the instrument guide including a first lumen extending through the instrument guide coaxially to the first axis, the instrument guide also including a second lumen extending through the instrument guide to define a second axis nonparallel to the first axis, the second axis extending through the same entry portal as the first axis, the instrument guide additionally including a third lumen extending through the instrument guide to define a third axis nonparallel to the first and second axes, the third axis extending through the same entry portal as the first and second axes, the third axis intersecting the first and second axes at a point spaced apart from the instrument guide, wherein the instrument guide is coupled to the base with at least an adjustable coupling configured to position the instrument guide at an adjustable height above the entry portal, the adjustable coupling including a sleeve on the instrument guide that is received in a collar on the base.

2. The apparatus of claim 1, in which the instrument guide includes an outer surface, distal from the entry portal, the first and second lumens extending through the surface, the surface shaped such that a distance along the first lumen between the surface and the target plane is substantially equal to a distance along the second lumen between the surface and the target plane.

3. The apparatus of claim 1, in which the first and second axes define a first plane and the second axis is angled at a first angle, in the first plane, with respect to the first axis, and in which the first and second axes are configured to intersect in the subject at or beyond the entry portal.

4. The apparatus of claim 1, in which a first angle between the first and second axes is selected at a predetermined value to provide a predetermined offset distance between intersection points of the first and second axes with a range plane, located beyond the entry portal, that is substantially orthogonal to the first axis.

5. The apparatus of claim 4, in which the adjustable coupling is configured to position the instrument guide at a height above the entry portal that obtains intersection of at least a portion of the target by the range plane.

6. The apparatus of claim 4, in which the predetermined offset distance exceeds a radius of the entry portal.

7. The apparatus of claim 1, in which the adjustable coupling includes a threaded coupling.

8. The apparatus of claim 1, in which the instrument guide includes a plurality of lumens through the instrument guide, the plurality of lumens including the first, second, and third lumens, the plurality of lumens configured to define corresponding axes passing through the entry portal, at least one of the axes being nonparallel to another of the axes.

9. The apparatus of claim 8, in which the axes corresponding to the plurality of lumens intersect a range plane beyond the entry portal, the range plane being substantially orthogonal to the first axis, and intersection points with the range plane of the axes corresponding to the lumens forming a scaled mirror image of intersection points between the axes and a plane through the instrument guide that is orthogonal to the first axis.

10. The apparatus of claim 9, in which the axes corresponding to the plurality of lumens are configured to substantially intersect about a single point in the subject adjacent to the entry portal.

11. The apparatus of claim 9, in which the apparatus includes a visualization portal configured to allow a user to view an instrument being inserted through at least one of the plurality of lumens into the subject.

12. The apparatus of claim 1, in which the instrument guide is rotatably coupled to the base to allow rotation of the instrument guide, with respect to the base, about the first axis when the instrument guide is oriented such that the first axis is orthogonal to the entry plane.

13. The apparatus of claim 12, in which at least one of the instrument guide and the base includes visual indicia providing information about a degree of rotation of the instrument guide with respect to the base.

14. The apparatus of claim 1, in which the base and the instrument guide are integrally formed of a customized fixed size and shape that is tailored to orient the first axis toward the target within the subject.

15. The apparatus of claim 1, in which the base and the instrument guide are adjustably coupled together to adjustably orient the first axis toward the target within the subject.

16. The apparatus of claim 15, further including a ball-and-socket adjustable coupling between the base and the instrument guide.

17. The apparatus of claim 15, in which the base and the instrument guide are adjustably coupled using at least one of:
a rotational coupling that allows rotation of the instrument guide about an axis that is substantially orthogonal to the entry portal; and
a saddle coupling that allows adjustment of an angle between the first axis and the axis that is substantially orthogonal to the entry portal.

18. The apparatus of claim 1, in which the base includes a viewing portal through which the entry portal is visible.

19. The apparatus of claim 1, further comprising:
a saddle that is rotatably coupled to the base about a rotation axis that is nonparallel to the axis of the entry portal, the saddle including a receptacle; and
wherein the instrument guide includes a ball that is rotatably received in the receptacle of the saddle to allow rotation of the instrument guide, with respect to the base, about the first axis when the instrument guide is oriented such that the first axis is orthogonal to the entry plane.

20. An apparatus comprising:
a base, sized and shaped to be secured in or about a pre-existing entry portal in a human or animal subject that includes a target within the subject beyond the entry portal, the entry portal defining an entry plane, and the target defining a target plane that is substantially parallel to the entry plane;
a saddle that is rotatably coupled to the base, the saddle defining a receptacle; and
an instrument guide moveably coupled to the saddle, the instrument guide including a first lumen with a first axis that extends through the instrument guide and the entry portal toward the target, the instrument guide further including a second lumen extending through the instrument guide to define a second axis nonparallel to the first axis, the second axis extending through the same entry portal as the first axis, the instrument guide further including a third lumen extending through the instrument guide to define a third axis nonparallel to the first and second axes, the third axis extending through the same entry portal as the first and second axes, the third axis intersecting the first and second axes at a point spaced apart from the instrument guide, wherein the instrument guide includes a ball that is rotatably received in the receptacle of the saddle, and wherein the instrument guide includes a sleeve that is adjustably received in the ball such that the instrument guide is adjustable in height relative to the base.

21. The apparatus of claim 1, wherein the first lumen is disposed between the second and third lumen.

22. The apparatus of claim 1, wherein the instrument guide includes a plurality of lumen including the first, second, and third lumen, and wherein every one of the plurality of lumen of the instrument guide intersect at a point spaced apart from the instrument guide.

23. The apparatus of claim 1, further comprising a saddle that is rotatably coupled to the base about a rotation axis that is nonparallel to the axis of the entry portal, the saddle coupling the instrument guide to the base.

* * * * *